US009295428B2

(12) United States Patent
Lian et al.

(10) Patent No.: US 9,295,428 B2
(45) Date of Patent: Mar. 29, 2016

(54) METHOD OF ENHANCING THE SIGNAL-TO-NOISE RATIO (SNR) OF MEASURED ELECTROCARDIOGRAM (ECG) SIGNALS AND A CARDIAC DEVICE FOR USE IN DETECTING HEARTBEATS

(71) Applicant: BIOTRONIK SE & Co. KG, Berlin (DE)

(72) Inventors: Jie Lian, Beaverton, OR (US); Garth Garner, Tigard, OR (US); Dirk Müssig, West Linn, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 257 days.

(21) Appl. No.: 13/973,418

(22) Filed: Aug. 22, 2013

(65) Prior Publication Data

US 2014/0088399 A1 Mar. 27, 2014

Related U.S. Application Data

(60) Provisional application No. 61/703,781, filed on Sep. 21, 2012.

(51) Int. Cl.
*A61B 5/04* (2006.01)
*A61B 5/00* (2006.01)
(Continued)

(52) U.S. Cl.
CPC ............. *A61B 5/7214* (2013.01); *A61B 5/0404* (2013.01); *A61B 5/04011* (2013.01);
(Continued)

(58) Field of Classification Search
CPC ...... A61B 5/04; A61B 5/0402; A61B 5/0408; A61B 5/0432; A61B 5/044; A61N 1/00; A61N 1/02; A61N 1/375
See application file for complete search history.

(56) References Cited

U.S. PATENT DOCUMENTS 5,891,048 A 4/1999 Nigam et al.
6,470,215 B1 10/2002 Kraus et al.
(Continued)

FOREIGN PATENT DOCUMENTS

EP 2 179 690 4/2010
EP 2 407 097 1/2012
WO 2006/115772 11/2006

OTHER PUBLICATIONS

European Search Report and Annex to the European Search Report on European Patent Application No. EP 13 18 0537, dated Dec. 19, 2013 (8 pages).

*Primary Examiner* — Christopher D Koharski
*Assistant Examiner* — Elizabeth K So
(74) *Attorney, Agent, or Firm* — Buchanan Ingersoll & Rooney PC

(57) ABSTRACT

A method of enhancing the signal-to-noise ratio (SNR) of measured electrocardiogram (ECG) signals is provided. The method includes the steps of providing at least three cardiac input signals derived from the measured ECG signals $S_1$ and forming a first estimate $U_1$ $S_2$ from each of at least three pairs of input signals. Moreover, the method includes the steps of forming a second estimate $U_2$ $S_3$ from each of at least three input signals; comparing $S_4$ the polarity and the amplitude of a first and second estimate $U_1$, $U_2$ to at least one threshold T; generating $S_5$ a composite signal X, wherein the polarity and the amplitude of the composite signal X depend on the result of the comparison; and using $S_6$ the generated composite signal X to produce an output signal with enhanced signal-to-noise ratio (SNR). Furthermore, a corresponding cardiac device is also provided.

14 Claims, 16 Drawing Sheets

(51) Int. Cl.
*A61B 5/0472* (2006.01)
*A61B 5/0432* (2006.01)
*A61B 5/0408* (2006.01)
*A61B 5/0404* (2006.01)
*A61B 5/0402* (2006.01)

(52) U.S. Cl.
CPC ......... *A61B5/04018* (2013.01); *A61B 5/04028* (2013.01); *A61B 5/0432* (2013.01); *A61B 5/0472* (2013.01); *A61B 5/04085* (2013.01)

(56) References Cited

U.S. PATENT DOCUMENTS

| | | | |
|---|---|---|---|
| 6,574,509 | B1 | 6/2003 | Kraus et al. |
| 6,622,043 | B1 | 9/2003 | Kraus et al. |
| 6,699,200 | B2 | 3/2004 | Cao et al. |
| 2001/0034487 | A1 | 10/2001 | Cao et al. |
| 2002/0068958 | A1* | 6/2002 | Bardy et al. ............ 607/5 |
| 2010/0312131 | A1 | 12/2010 | Naware et al. |
| 2011/0130669 | A1 | 6/2011 | Garner et al. |

\* cited by examiner

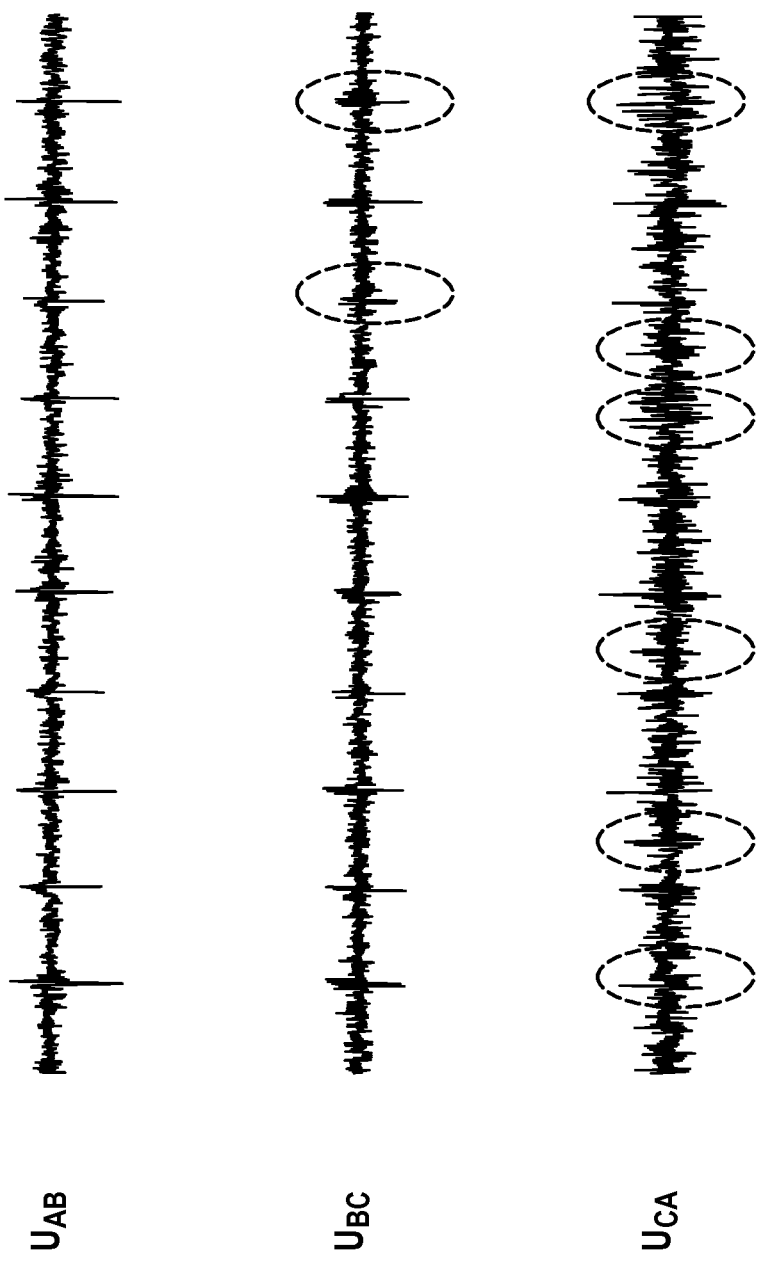

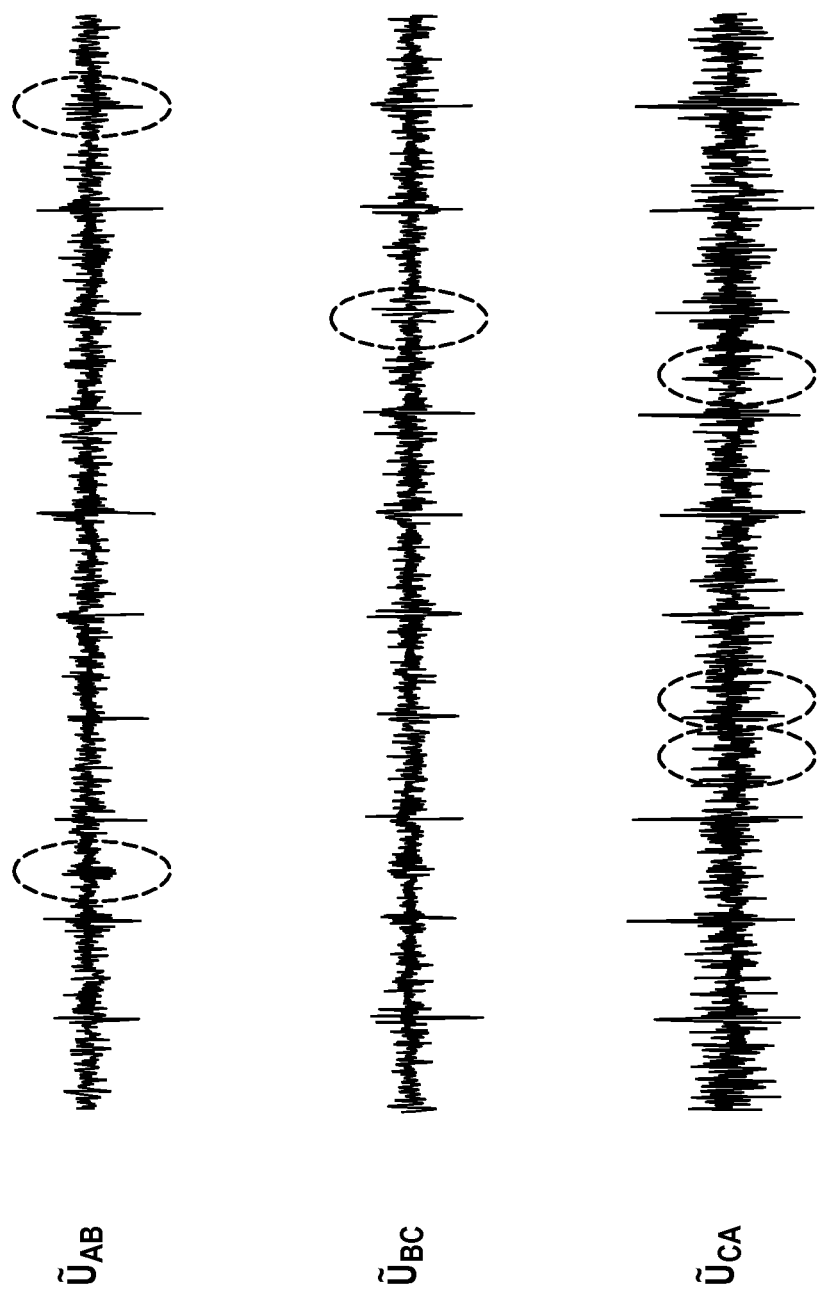

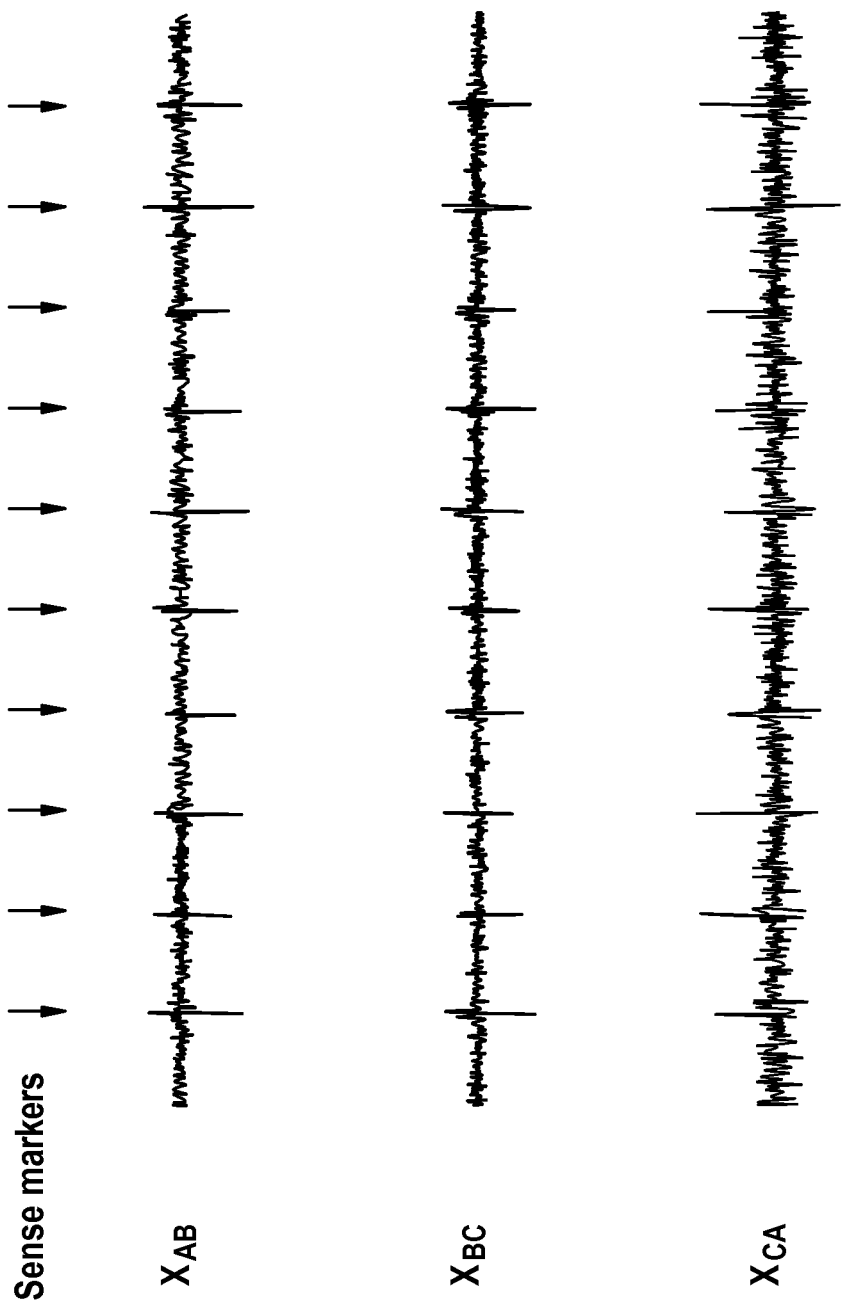

METHOD OF ENHANCING THE SIGNAL-TO-NOISE RATIO (SNR) OF MEASURED ELECTROCARDIOGRAM (ECG) SIGNALS AND A CARDIAC DEVICE FOR USE IN DETECTING HEARTBEATS

CROSS-REFERENCE TO RELATED APPLICATIONS

This patent application claims the benefit of U.S. Provisional Patent Application No. 61/703,781, filed on Sep. 21, 2012, which is hereby incorporated by reference in its entirety.

TECHNICAL FIELD

The present invention generally relates to medical cardiac devices that measure cardiac electrical signals, analyze the said cardiac electrical signals, and detect the cardiac beat for each cardiac cycle. More particularly, the present invention relates to a method and a cardiac device for robust cardiac beat detection from surface ECG or subcutaneous ECG signals by improving the signal to noise ratio of ECG signals or subcutaneous ECG signals.

BACKGROUND

A standard 12-lead electrocardiogram (ECG) is a representation of the heart's electrical activity recorded from sensing electrodes on the body surface. It is a standard tool for evaluating the cardiac function. Normal ECG tracing is comprised of different waves that represent the sequence of depolarization and repolarization of the atria and ventricles. For example, a P wave represents atrial depolarization, a QRS complex represents ventricular depolarization, and a T wave represents ventricular repolarization. From these ECG waves, a plurality of intervals can be calculated that reflect the cardiac conduction properties (e.g., P wave duration, PR interval, QRS duration) and the repolarization properties (e.g., QT interval), heart rate (e.g., PP or RR intervals), etc. Collectively, these ECG waves and durations contain important diagnostic information regarding the underlying cardiac condition of a patient.

However, many patients have intermittent spontaneous cardiac arrhythmias, for example sinus bradycardia, non-sustained ventricular tachycardia or paroxysmal atrial fibrillation events, which may not be recorded during their clinic visits. In order to capture these infrequent arrhythmia episodes, external ECG monitoring devices, such as Holters, are frequently prescribed to continuously monitor the patient's ECG. However, Holter recording has two inherent drawbacks. First, the memory capacity is limited, and most commercially available Holter machines can only record 24-hr or 48-hr surface ECG. Second, the use of skin electrodes is inconvenient and uncomfortable for the patient, and is a significant source of measurement noise due to loose contact, muscle movement, and environmental factors. Consequently, the diagnostic yield of a Holter ECG is very limited.

To overcome these shortcomings, implantable loop recorder monitors have been introduced. By implanting a small device with sensing electrodes underneath the skin, the subcutaneous ECG monitor can record subcutaneous ECG which resembles the surface ECG. The subcutaneous ECG monitor can be configured as an implantable loop recorder (ILR), so that it continuously records newly acquired subcutaneous ECG while discarding the old recordings. When experiencing symptoms, a patient can use a handheld device which communicates with the subcutaneous device to trigger a snapshot of the recordings. Alternatively, the implantable cardiac device can be programmed to automatically trigger a snapshot of the subcutaneous ECG upon detection of an arrhythmic episode. The recorded snapshots can then be transmitted over the wired or wireless network to the physician's office for clinical review. Because the loop recorder continuously refreshes its memory, it can be carried for long periods of time. Thus, it is ideal for capturing ECG traces of infrequent episodes such as syncope. Recently, subcutaneous ECG recording has also become a useful means to monitor the cardiac rhythm after ablation of atrial fibrillation, to determine the ablation efficacy and adjust therapeutic schemes.

Irrespective of the ECG recording apparatus (e.g., ECG machines, bedside ECG monitors, Holter ECG monitors, subcutaneous ECG devices, etc.), reliable beat detection is the prerequisite for further ECG processing and clinical diagnosis. Despite decades of research, ECG beat detection has remained as a technical challenge. On one hand, many factors can cause over-sensing (false detection) of cardiac beats, such as, for example, large T waves, wider QRS complexes, muscle noise, electromagnetic interference (EMI), and the like. On the other hand, under-sensing (missed detection) of cardiac beats are also common for ECG signals that have a small signal-to-noise ratio. Existing methods for real-time ECG beat detection are either computationally complex, and therefore not suitable for the implementation in an embedded system, or oversimplified, so that they, for example, rely solely on ECG metrics such as peak amplitude, peak slope, etc., with or without adaptive sensing threshold, and thus they result in unsatisfactory performance.

Therefore, there is a need to provide an apparatus and a method for more accurate and efficient detection of cardiac beats based on surface ECG or subcutaneous ECG recordings.

In addition, there is also a need to optimize the geometric shape of subcutaneous ECG monitors or cardiac devices in general. On one hand, subcutaneous ECG monitors preferably should have a small size to facilitate implantation. On the other hand, large inter-electrode distance is preferred to facilitate signal sensing. No existing subcutaneous ECG monitor known in the state of art meets both of these two seemingly contradictory requirements. For example, two existing products, namely, Reveal ILR manufactured by Medtronic and Confirm ILR manufactured by St Jude Medical, both have an elongated rectangular shape. Each device has two electrodes located at the outer surface of the device along the long axis. Evidently, the inter-electrode distance is limited by the length of the device. The Sleuth ILR manufactured by Transoma has the shape of a typical pacemaker. One electrode is located at the outer surface of the device can, and another electrode is located at the tip of a wire antenna which is connected to the device header. Although this design can increase the inter-electrode distance, it also increases the difficulty of the implantation of the device due to the need to straighten the flexible wire antenna and secure its position.

Furthermore, all these mentioned products have only one sensing vector. The shape and size of the devices make it difficult to add additional electrodes. From U.S. Pat. No. 6,699,200, a boomerang shaped implantable loop recorder design having three sensing channels is known. However, this design has limited options to arrange the sensing electrodes (two electrodes at the end of the wings and one electrode in the center). In addition, the bending of the device between two wings makes it difficult to insert the device into the pocket. Moreover, the shape is not ergonomic, and the device may be easy to move in the pocket, causing change of the sensing vectors. Similar limitations also apply to the triangular shaped ILR disclosed in the U.S. Publication No. 2010/0312131.

For at least the reasons given above, there is a need to optimize the shape of the subcutaneous ECG monitor so that it has a small size and is easy for implantation, allows placement of multiple sensing electrodes with large inter-electrode distance, provides flexible sensing vectors, has an ergonomic shape that can give an improved cosmetic appearance after implantation, and can be securely anchored in the pocket and is less prone to movement.

The present invention is directed toward overcoming one or more of the above-identified problems.

SUMMARY

According to the present invention, a method of enhancing the signal-to-noise ratio (SNR) of measured electrocardiogram (ECG) signals is provided. The method comprises the steps of providing at least three cardiac input signals derived from the measured ECG signals and forming a first estimate $U_1$ from each of at least three pairs of input signals. Moreover, the method comprises the steps of forming a second estimate $U_2$ from each of at least three input signals; comparing the polarity and the amplitude of a first and second estimate $U_1$, $U_2$ to at least one threshold T; generating a composite signal X, wherein the polarity and the amplitude of the composite signal X depend on the result of the comparison; and using the generated composite signal X to produce an output signal with enhanced signal-to-noise ratio (SNR).

The advantage of such a method is that it enables the execution of a so called XASA (Cross-check and Adjustemt of Signal Amplitude)-algorithm within the processing and evaluation of measured electrocardiogram (ECG) signals, wherein the XASA-algorithm is based on vector arithmetic. Through this XASA-algorithm, a first and second estimate $U_1$ and $U_2$ from each of at least three pairs of input signals can be evaluated regarding their polarity, amplitude, relation to each other and their relation to a predefined threshold T, thus enabling a significant improvement in the signal-to-noise ratio (SNR) of the output signal. Expressed in other words, composite signals X, generated within the execution of the method according to the present invention as a result of applying a XASA-algorithm on a first and second estimate $U_1$, $U_2$ from each of at least three pairs of input signals, show significantly enhanced signal components while the noise components of the composite signals X are significantly reduced.

In a preferred embodiment, the first estimate $U_1$ is a differential signal $\tilde{U}$ and the second estimate $U_2$ is an averaged signal $\overline{U}$ formed by using a weighted moving average filter. Since in many embodiments of the method according to the present invention, the measured electrocardiogram (ECG) signals are time-multiplexed, it is advantageous to use a differential signal $\tilde{U}$ as a first estimate $U_1$, wherein in the differential signal $\tilde{U}$, signals measured at points in time that are close to the point in time of the signal that is to be approximated are differentiated. Furthermore, through the use of an averaged signal $\overline{U}$ for a second estimate $U_2$, formed by applying a weighted moving average filter on the measured electrocardiogram (ECG) signals, the received second estimates $U_2=\overline{U}$ are better aligned to the first estimates $U_1=\tilde{U}$.

Preferably, within the step of comparing, the first and second estimate $U_1$ and $U_2$ are compared to an upper threshold UT and/or a lower threshold LT. Through such an embodiment of the inventive method, the signal space for the first and second estimate $U_1$ and $U_2$ and for the composite signal X can be divided into three zones by the upper and lower threshold UT and LT. The signal space can, for example, be divided into a positive zone Z+, a null zone Z0, and a negative zone Z−. The composite signal X can then be set to a certain value, depending on the zone a first and second estimate $U_1$ and $U_2$ fall in.

Preferably, the lower threshold LT and the upper threshold UT are symmetric around the baseline of the measured electrocardiogram (ECG) signals and/or predefinable by a user and/or automatically adjusted based on the moving average of the peaks of the absolute amplitudes of previously measured QRS complexes that are detected within the previously measured electrocardiogram (ECG) signals. Through such embodiments of the inventive method, the efficiency of the inventive method is increased which is expressed in an enhanced signal-to-noise ratio (SNR) of the output signal.

In a preferred embodiment, a composite signal X=0 is generated if the corresponding first estimate $U_1$ is lower than the lower threshold LT and the corresponding second estimate $U_2$ is greater than the upper threshold UT, or if the corresponding first estimate $U_1$ is greater than the upper threshold UT and the corresponding second estimate $U_2$ is lower than the lower threshold LT. This condition implies that the first and second estimates $U_1$ and $U_2$ have opposite phases. This large discrepancy suggests possible noise interference in the input signals.

In another preferred embodiment, if a first and second estimate $U_1$, $U_2$ are both greater than or equal to the lower threshold LT and both lower than or equal to the upper threshold UT, a corresponding composite signal $X=U_1$ is generated if the absolute value of the corresponding second estimate $U_2$ is greater than the absolute value of the corresponding first estimate $U_1$, or a corresponding composite signal $X=U_2$ is generated if the absolute value of the corresponding first estimate $U_1$ is greater than or equal to the absolute value of the corresponding second estimate $U_2$. This condition implies that both the first and second estimates $U_1$ and $U_2$ are near the baseline of the measured electrocardiogram (ECG) signals, so the one that is closer to the baseline of the measured electrocardiogram (ECG) signals, for example the one with the smaller absolute amplitude, is chosen as the output amplitude.

Preferably, a composite signal X equal to the arithmetic mean of a corresponding first and second estimate $U_1$, $U_2$ is generated if the corresponding second estimate $U_2$ is greater than or equal to the lower threshold LT and lower than or equal to the upper threshold UT, while the corresponding first estimate $U_1$ is either greater than the upper threshold UT or lower than the lower threshold LT, or if a corresponding first estimate $U_1$ is greater than or equal to the lower threshold LT and lower than or equal to the upper threshold UT, while the corresponding second estimate $U_2$ is either greater than the upper threshold UT or lower than the lower threshold LT. This condition implies that there is modest discrepancy between the first and second estimate $U_1$ and $U_2$, thus their average value is chosen as the output amplitude.

In a preferred embodiment, if a first and second estimate $U_1$ and $U_2$ are both greater than the upper threshold UT or both lower than the lower threshold LT, a corresponding composite signal $X=U_2$ is generated if the absolute value of the corresponding second estimate $U_2$ is greater than the absolute value of the corresponding first estimate $U_1$, or a corresponding composite signal $X=U_1$ is generated if the absolute value of the corresponding first estimate $U_1$ is greater than or equal to the absolute value of the corresponding second estimate $U_2$. This condition implies that both the first and second estimates $U_1$ and $U_2$ have a consistent phase, suggesting it belongs to a signal component, so the one that has the larger absolute amplitude is chosen as the output amplitude.

Furthermore, a cardiac device for use in detecting heartbeats, to which at least three external sensing electrodes are attachable to provide at least three analog voltage input signals, is provided. The cardiac device comprises an electrocardiogram (ECG) sensing unit for use in producing digital signals from the analog voltage input signals. The electrocardiogram (ECG) sensing unit comprises a multiplexer and a plurality of signal processing units. Furthermore, the cardiac device comprises a controller having interconnected parts including a programmable microprocessor, a battery, a memory and a system clock, wherein the battery supplies power to the cardiac device. According to the present invention, the cardiac device comprises a further processing unit and is designed to execute a method according to present invention using the further processing unit. Such a cardiac device is able to apply a XASA-algorithm on the at least three analog voltage input signals in order to produce an output signal with enhanced signal-to-noise ratio (SNR).

In a preferred embodiment, the cardiac device comprises a rounded head with a length of $d_1$ and a rounded tail with a length of $d_2$, wherein $d_1$ is smaller than $d_2$.

Preferably, $d_1$ and $d_2$ follow the equation $(d_1+d_2)/d_2 \approx d_2/d_1$, wherein $d_2/d_1 \approx (1+\sqrt{5};)/2 \approx 1.6$. In a more preferred embodiment, $(d_1+d_2)/d_2$ is equal to $d_2/d_1$ wherein $d_2/d_1=1.6$. In another preferred embodiment, $(d_1+d_2)/d_2$ is equal to $d_2/d_1$ wherein $d_2/d_1=1.6+/-y$ wherein $y \in [0, 0.2]$ and $y \in IR$. Such an equation sets the relationship between $d_2$ and $d_1$ to the golden ratio, enabling the realization of an easily implantable cardiac device with a small size.

Preferably, the cardiac device has an asymmetric geometry and resembles a spiral shape, wherein the bottom contour of the cardiac device has a shape that approximates the Fibonacci spiral, while the top contour of the cardiac device follows a spiral shape that is rounded at the head and the tail of the cardiac device. Such an embodiment enables a great distance between the external sensing electrodes that are attached to the cardiac device, thus enabling a stable Einthoven's triangle.

In a further development of this embodiment, at least three external sensing electrodes are respectively located in the top of the head of the cardiac device, in the bottom of the cardiac device and at the end of the tail of the cardiac device. Through such an embodiment of the cardiac device, the three sensing electrodes have a large distance to each other. If the cardiac device in this embodiment is transplanted in a patient's chest, two of the sensing electrodes form the highest part of the device, while the remaining sensing electrode forms the lowest part of the cardiac device.

In another embodiment, the cardiac device has an egg-oval shape that is symmetric to a first centerline C1, wherein the head of the cardiac device is wider than the tail of the cardiac device.

In a further development of this embodiment, the cardiac device has a flat back and a spiral shaped front or a flat front.

In a further development of this embodiment, the cardiac device comprises four external sensing electrodes, wherein two of the external sensing electrodes are respectively located with the greatest distance possible from one another, in the tail and the head of the cardiac device, at the intersection points of the first centerline C1 with the circumference of the cardiac device. The other two of the external sensing electrodes are located in the top and bottom of the cardiac device, positioned at the intersection points of a line L1 with the circumference of the cardiac device, wherein the line L1 is orthogonal to the first centerline C1. Preferably, the line L1 is crossing the center of gravity of the cardiac device.

Preferably, the cardiac device is an implantable subcutaneous ECG monitoring cardiac device, which is implantable in the chest of a patient and further comprises an RF unit for use in communicating signals to external parties.

Further features, aspects, objects, advantages, and possible applications of the present invention will become apparent from a study of the exemplary embodiments and examples described below, in combination with the figures, and the appended claims.

The details of the present invention can be understood from the following drawings and the corresponding text descriptions.

DESCRIPTION OF THE DRAWINGS

FIG. 8 shows an example of three channels of time-multiplexed digital subcutaneous ECG signals $U_{AB}$, $U_{BC}$ and $U_{CA}$.

FIG. 9 shows the signals $\tilde{U}_{AB}$, $\tilde{U}_{BC}$, $\tilde{U}_{CA}$ that are estimated from the time-multiplexed differential signals $U_{AB}$, $U_{BC}$ and $U_{CA}$.

FIG. 10 shows the composite signals $X_{AB}$, $X_{BC}$, and $X_{CA}$ which are outputted by the XASA-units and respectively constructed from the first estimated signals $\tilde{U}_{AB}$, $\tilde{U}_{BC}$, $\tilde{U}_{CA}$, and the second estimated signals $\tilde{\tilde{U}}_{AB}$, $\tilde{\tilde{U}}_{BC}$ and $\tilde{\tilde{U}}_{CA}$.

DETAILED DESCRIPTION

Figure 1:
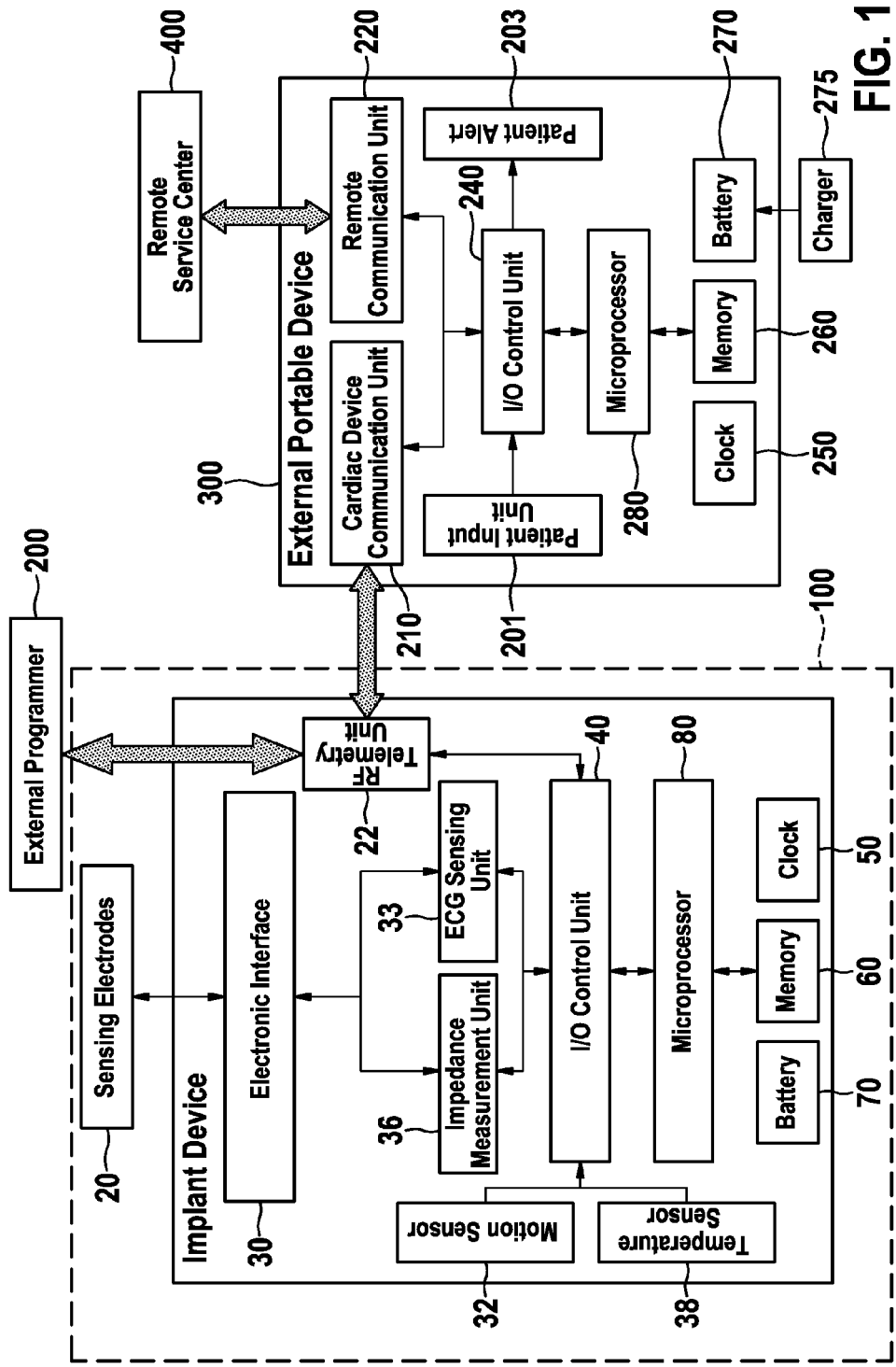
FIG. 1 shows a block diagram of an implantable subcutaneous ECG monitoring cardiac device for subcutaneous ECG monitoring and its interfaces with an external programmer and an external portable device, which further communicates with the remote service center.

FIG. 1 shows a block diagram of an implantable subcutaneous ECG monitoring cardiac device 100 for subcutaneous ECG monitoring and its interfaces with an external programmer 200 and an external portable device 300, which further communicates with the remote service center 400.

The cardiac device 100 consists of an electronic circuitry that is hermetically sealed inside a Can, which is made from a biocompatible conductive material such as, for example, titanium. Optionally, one or more subcutaneous leads are connected to respective non-conductive headers which are attached to the Can. Three or more sensing electrodes 20, which are electrically isolated from one another, are mounted over the outer surface of the Can, or outside the header (if available), or at the distal end of the leads (if available). For subcutaneous ECG recording, one or more pairs of sensing electrodes 20 form a set of sensing vectors, wherein each pair of sensing electrodes 20 is separated by an inter-electrode distance that is preferably greater than 3 cm.

Enclosed inside the hermetically sealed Can, a microprocessor 80 and associated circuitry make up a controller of the cardiac device 100. The cardiac device 100 is powered by a battery 70, and maintains an internal clock 50 for timing operations. The microprocessor 80 communicates with a memory 60 via a bi-directional data bus. The memory 60 typically comprises a ROM or RAM for program storage and a RAM for data storage.

The sensing electrodes 20 are first connected to an electronic interface 30 that preferably includes a feed through circuitry for noise reduction, a high voltage protection circuitry, switch network circuitry for sensing channel selection, and front-end analog filters, as is well known in the field. The configurations of the circuitry of the electronic interface 30 (e.g., filter settings, sensing channel selection, etc.) can be programmed by the microprocessor 80.

The microprocessor 80 connects to an I/O control unit 40 to manage the input and output of the cardiac device 100. One input signal is the subcutaneous ECG picked up by the sensing electrodes 20. After being pre-processed by the circuitry of the electronic interface 30, the subcutaneous ECG signal is further processed by the ECG sensing unit 33, which may include amplifiers, analog-to-digital converters, digital filters, etc., as known in the art.

Another input signal is the impedance-signal measured between the sensing electrodes 20 by an impedance measurement unit 36. By injecting a small constant current (e.g., 100 uA, preferably biphasic) between two sensing electrodes 20 while measuring the voltage difference between the same or a different pair of sensing electrodes 20, the impedance may be calculated, using Ohm's law, as the ratio of the measured voltage difference and the injecting current strength to the value of the injected current. As known in the art, the impedance-signal provides useful information about the integrity of the sensing channel 6. In addition, a continuously measured impedance signal sensed by an impedance measurement unit 36 may be further processed by the microprocessor 80 to extract other aspects of the physiological status of the patient, such as, for example, the respiration rate.

Other types of biological signals measured by specific sensors can also serve as input to the cardiac device 100. For example, an on-board accelerometer can serve as a motion sensor 32 that provides a patient's activity signal to the cardiac device 100, and a temperature sensor 38, either located on-board or embedded in a lead, may provide a subcutaneous temperature signal to the cardiac device. Other types of input signals include, but are not limited to, a subcutaneous pressure signal measured by a pressure sensor, an acoustic signal measured by an acoustic sensor, a subcutaneous pH signal measured by a pH sensor, and the like.

By running a program stored in the memory 60, the microprocessor 80 also sends instructions to the ECG sensing unit 33, the impedance measurement unit 36, and other input measurement units to control how these acquire respective signals by adjusting parameters, such as gain, offset, filter settings, sampling frequency, sampling resolution, and the like.

The acquired biological signals are then stored in the memory 60 of the cardiac device 100 and analyzed by the microprocessor 80 by running programmed algorithms. For example, the microprocessor 80 continuously analyzes the acquired subcutaneous ECG signals to detect the peak of a QRS complex. Such QRS peak detection can be achieved by many different means. One typical embodiment is to use an Auto-Sensing algorithm that applies a detection hold-off period after each peak detection, then automatically adjusts the sensing threshold, which is adaptive to the measured peak amplitude of the QRS complex and then varies in accordance with a predetermined time dependence. One exemplary Auto-Sensing algorithm has been disclosed in U.S. Pat. No. 5,891,048. In the present invention, however, a more robust ECG beat detection method will be described in details below.

Accordingly, the cardiac device 100 measures intervals between pairs of adjacent peaks in the detected QRS complexes. These measured intervals, termed RR intervals, may be stored in the memory 60 of the cardiac device 100 according to predefined storage modes. One typical mode is the queue-loop mode, meaning the measured RR intervals are stored in a predefined memory space, and while the allocated memory space is full, the newly measured RR intervals replace the oldest stored RR interval data. Another typical mode is the snapshot mode, meaning the measured RR intervals are stored in a predefined memory space, and while the allocated memory space is full, the newly measured RR intervals are not stored until the microprocessor 80 decides to store another episode of RR intervals. Yet another typical mode is the mixed mode, in which one or more segments of allocated memory space store the RR intervals in queue-loop mode, whereas one or more segments of separately allocated memory space store the RR intervals in snapshot mode.

Similarly, the microprocessor 80 may also continuously analyze the acquired subcutaneous ECG signals to measure other metrics of the QRS complex, such as the width of the QRS complex, the positive or negative peak amplitude of the QRS complex, the absolute area under the QRS complex, the maximum positive or negative slopes of the QRS complex, the dominant frequency component of the QRS complex, the complexity measures (e.g., sampled entropy) of the QRS complex, and so on. Likewise, the time series of these measured metrics are stored in the memory 60 of the cardiac device 100 for further analysis.

The cardiac device 100 also includes a radio-frequency (RF) telemetry unit 22. The RF telemetry unit 22 may be of the type well known in the art for conveying various information obtained from the cardiac device 100 to an external programmer 200, or for receiving programming parameters from the external programmer 200 and then conveying the parameters to the cardiac device 100. In one embodiment, the external programmer 200 interrogates the cardiac device 100 to obtain a status (for example, the status of the battery 70 or the impedance of the sensing channel 6) of the cardiac device 100 or to obtain data recorded by the cardiac device 100, such as, for example, the peak amplitude of the QRS complexes, statistics of measured RR intervals, and the like. In another embodiment, the external programmer 200 may be used to activate or deactivate selected algorithms or to update programmable parameters of the cardiac device 100.

In addition, the external portable device 300 to be described hereinafter, may also communicate bi-directionally with the cardiac device 100 through the RF telemetry unit 22. Preferably, the data that may be received from or sent to the external portable device 300 are more limited as compared to the data that may be received from or sent to the external programmer 200.

In a preferred embodiment, data transmitted from the external portable device 300 to the cardiac device 100 may be in the form of simple commands, such as, for example, "trigger a snapshot of the acquired subcutaneous ECG", or "retrieve most recently diagnostic information from the cardiac device 100". These commands set the cardiac device 100 into one of a number of modalities, wherein each modality is determined and controlled by parameters that can only be selected by a physician operating the external programmer 200 using secure password or codes.

Data transmitted from the cardiac device 100 to the external portable device 300 preferably include a simple acknowledgment to confirm receiving the commands from the external portable device 300, and signals warning of the detection of abnormal conditions, such as atrial fibrillation (AF), high ventricular rate (HVR), low ventricular rate (LVR), abnormal sensing impedance, abnormal temperature, and so on. Other diagnostic information, such as the AF burden, the frequency of ectopic beats, snapshots of RR intervals or subcutaneous ECG, and the like, may also be transmitted to the external portable device 300. Preferably, the external programmer 200 is operated by a physician who uses a secure password or codes to control the enable or disable condition as well as the amount of data that can be transmitted from the cardiac device 100 to the external portable device 300.

The external portable device 300 shown in FIG. 1 has a power source, such as a lithium battery 270, which provides power to the electrical components of the external portable device 300. The battery 270 is chargeable when it is connected to an external charger 275. The external portable device 300 also maintains an internal clock 250 for timing its operations. The overall functioning of the external portable device 300 is controlled by its microprocessor 280, which reads and performs instructions stored in its associated memory 260. The instructions stored in the memory 260 preferably include instructions defining a communication protocol compatible with the cardiac device 100, and instructions defining a communication protocol compatible with the remote service center 400.

The microprocessor 280 of the external portal device 300 communicates with an I/O control unit 240 to read patient input commands from a keypad, press switches or any other patient input unit 201. In an exemplary embodiment, one subset of the patient input commands entered in the patient input unit 201 is designed to configure the external portable device 300, for example, to turn on or off certain outputs as described hereinafter, or to select specific communication protocols. Another subset of the patient input commands entered in the patient input unit 201 is designed to establish communication between the external portable device 300 and the remote service center 400 through a remote communication unit 220. For example, patient's input entered in the patient input unit 201 can command the external portable device 300 to transmit diagnostic information (retrieved from the cardiac device 100) to the remote service center 400, and wait to receive acknowledgement. The third subset of the input commands entered in the patient input unit 201 is designed to establish communication between the external portable device 300 and the cardiac device 100 through a cardiac device communication unit 210. For example, patient's input entered in the patient input unit 201 may command the external portable device 300 to transmit corresponding signals to the cardiac device 100 to trigger recording a snapshot of the subcutaneous ECG, to retrieve diagnostic information from the cardiac device 100, etc. The cardiac device communication unit 210 also receives the acknowledgement and related diagnostic information sent from the cardiac device 100, and conveys these data to the microprocessor 280 for storage in the memory 260.

According to one exemplary embodiment of the present invention, upon receiving a predefined warning signal from the cardiac device 100 (e.g., detection of AF, HVR, LVR, abnormal sensing impedance, abnormal temperature, etc.), the microprocessor 280 of the external portable device 300 communicates with the I/O control unit 240 to generate output in the form of a patient alert 203 that is perceptible by the patient. Such a patient alert 203 may be in the form of a visible message, for example, by illuminating a continuous or blinking light emitting diode (LED); a text message displayed in a liquid crystal display (LCD); an audible message such as beep, ringing tone, or pre-recorded voice message played through a speaker; or in the form of discernible mechanical vibration produced by a vibrator. According to the patient's preference, one or multiple types of warning messages may be respectively turned on or off. For example, at night, a visible warning message may be turned on while an audible warning message is turned off if the patient chooses not to be disturbed during sleep even if the cardiac device 100 detects AF. In addition to generating warning messages as a patient alert 203, some diagnostic information that is received from the cardiac device 100 and stored in the memory 260 (e.g., the heart rate) may also be provided to the patient in the form of visual or audible messages.

The external portable device 300, via its remote communication unit 220, may further communicate with the remote service center 400. Such long-range communication apparatus may be, for example, in the form of a mobile radio network, a fixed-line telecommunication network, or the internet, as is well known in the art. Examples of such long-range communication apparatus have been taught in U.S. Pat. No. 6,470,215, U.S. Pat. No. 6,574,509 and U.S. Pat. No. 6,622,043.

In one embodiment, the external portable device 300 transmits status information pertaining to the cardiac device 100, (for example, the status of the battery 70 of the cardiac device 100 or the sensing impedance) as well as relevant diagnostic information (e.g., AF burden, ectopic beat frequency, etc.) to the remote service center 400 according to a predefined transmission frequency and schedule (e.g., every night at midnight). In yet another embodiment, the external portable device 300 communicates with the remote service center 400 in a trigger mode, for example, upon receiving a warning signal from the cardiac device 100, or upon receiving a patient trigger. In such cases, the external portable device 300 transmits critical diagnostic information stored in the memory 260 of the external portable device 300 (e.g., AF burden, mean heart rate, subcutaneous ECG snapshot) to the remote service center 400.

The remote service center 400 receives the information via compatible communication protocols, then returns an acknowledgement to the external portable device 300, which may generate visible or audible output messages, indicating receipt of the acknowledgement. The data received by the remote service center 400 is stored in a central database, and may be promptly presented to the patient's physician or to a responsible expert via fax, email, or text messaging, as is customary in the art, or via similar or other means of communication. By reviewing the received diagnostic information, the physician can evaluate the patient's condition and provide expert advice to a patient who wishes to consult the physician before taking any action in response to the warning signals generated by the external portable device 300.

A novel method and apparatus for cardiac beat detection from subcutaneous ECG recordings that may be obtained using the cardiac device 100 shown in FIG. 1 is disclosed hereinafter. It shall be understood that the same principles are also applicable to cardiac beat detection from surface ECG recorded using conventional ECG machines, bedside ECG monitors, Holter ECG devices, automatic external defibrillators, and the like.

According to a preferred embodiment of the present invention, at least three sensing electrodes 20 are preferably connected to the input channels 6 of the cardiac device 100 to measure the subcutaneous ECG. The three sensing electrodes 20 are implanted in a patient's chest so that the sensing electrodes 20 are spatially separated, preferably by an inter-electrode distance exceeding 3 cm for each pair.

Figure 2:
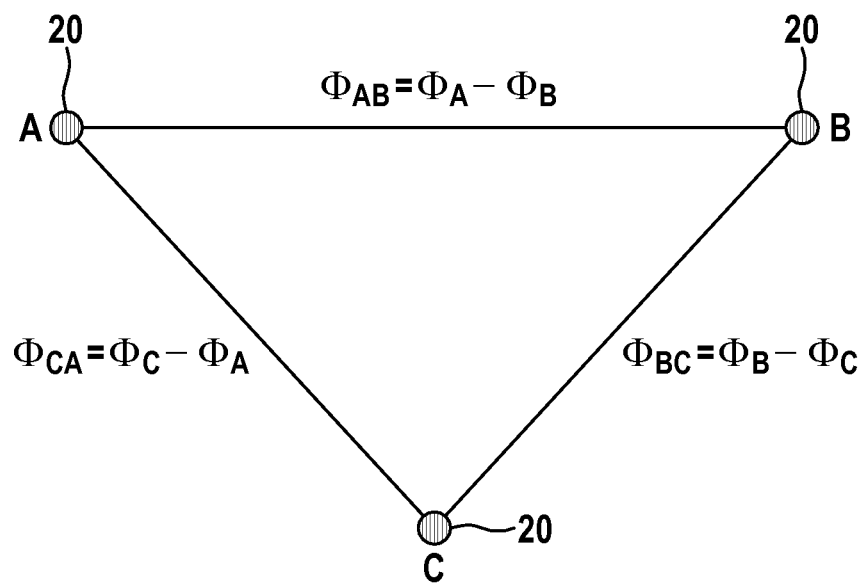
FIG. 2 shows a schematic drawing of three spatially distributed sensing electrodes that are capable to measure ECG or subcutaneous signals from three sensing vectors.

FIG. 2 shows a schematic drawing of three spatially distributed sensing electrodes 20 that are capable to measure ECG or subcutaneous signals from three sensing vectors.

As illustrated in FIG. 2, three sensing electrodes 20, labeled as A, B, and C, arranged in a triangle, as is commonly done, measure three focal subcutaneous electric potentials $\Phi_A$, $\Phi_B$, and $\Phi_C$, respectively. These three sensing electrodes 20 form three sensing vectors or leads that form a triangle. Specifically, the sensing electrodes 20 labeled A and B form lead AB that measures $\Phi_{AB}$, which is the voltage difference between $\Phi_A$ and $\Phi_B$. Similarly, the sensing electrodes 20 labeled B and C form lead BC that measures $\Phi_{BC}$, which is the voltage difference between $\Phi_B$ and $\Phi_C$. Likewise, the sensing electrodes 20 labeled C and A form lead CA that measures $\Phi_{CA}$, which is the voltage difference between $\Phi_C$ and $\Phi_A$. Hence, the triangular configuration for voltage measurement shown in FIG. 2 provides at least three subcutaneous ECG signal input channels 6 for the subcutaneous cardiac device 100.

Figure 3:
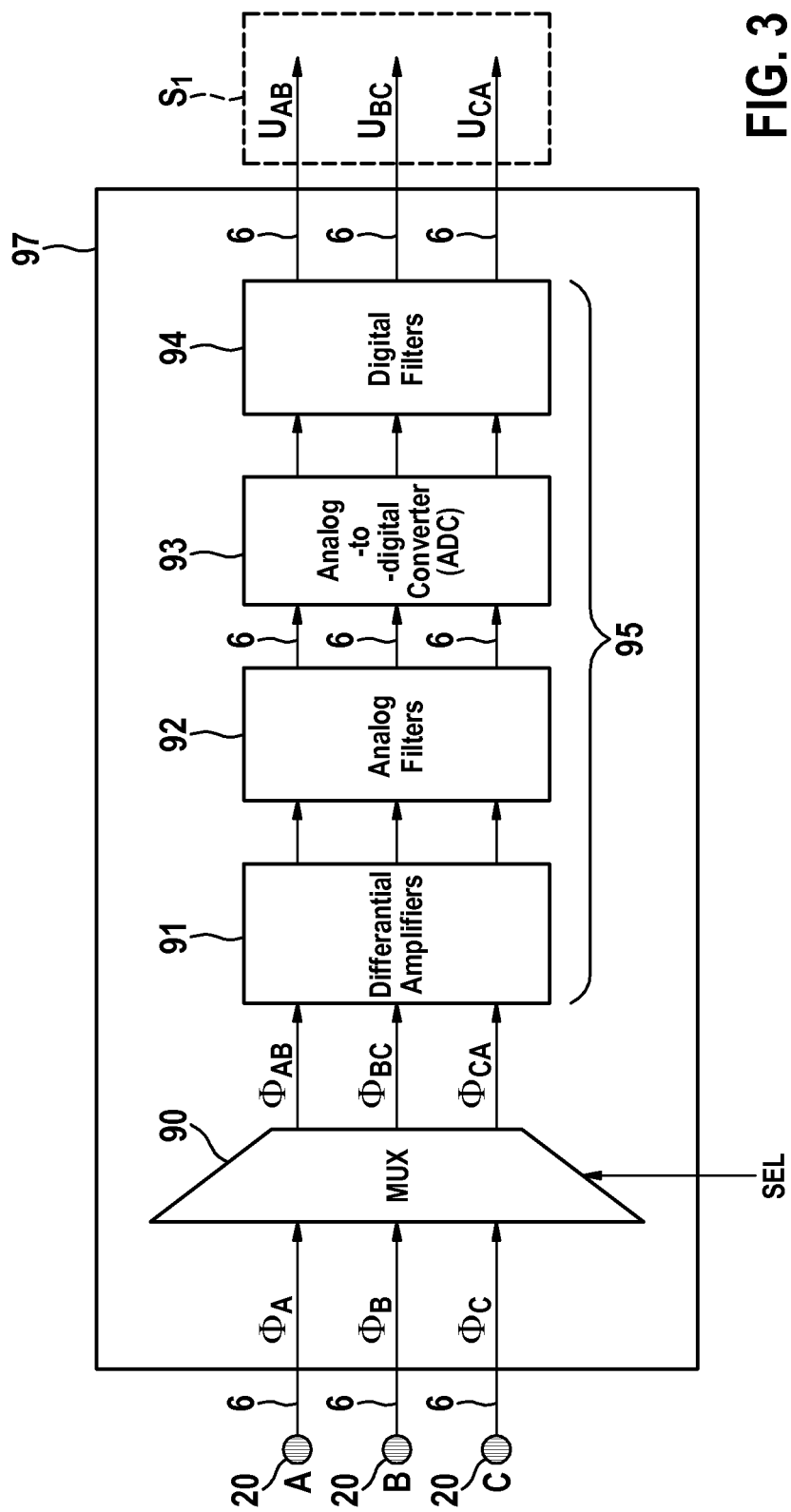
FIG. 3 shows a simplified block diagram of an electrocardiogram (ECG) sensing unit as the front-end of the cardiac device that includes a multiplexer and a plurality of signal processing units.

FIG. 3 shows a simplified block diagram of an electrocardiogram (ECG) sensing unit 97 as the front-end of the cardiac device 100 that includes a multiplexer 90 and a plurality of signal processing units 95. The electrocardiogram (ECG) sensing unit 97 combines the electronic interface 30 and the ECG sensing unit 33 of FIG. 1. The electrocardiogram (ECG) sensing unit 97 or the front end receives the analog voltage signals from three sensing electrodes 20 and generates three channels 6 of multiplexed digital output. In this FIG. 3, the front-end circuit consists of five signal processing layers: the multiplexer 90, the differential amplifiers 91, the analog filters 92, the analog-to-digital converter (ADC) 93, and the digital filters 94. Expressed in other words, the electrocardiogram (ECG) sensing unit 97 of the cardiac device 100 comprises a multiplexer 90 and plurality of signal processing units 95. In this embodiment of the present invention, the electrocardiogram (ECG) sensing unit 97 comprises four signal processing units 91, 92, 93 and 94.

As shown in FIG. 3, three subcutaneous sensing electrodes 20 labeled A, B, C measure the focal subcutaneous electric potentials $\Phi_A$, $\Phi_B$, and $\Phi_C$, respectively, and are connected to the input of a multiplexer 90. The multiplexer 90 is controlled by the microprocessor 80 of the cardiac device 100, which divides the time domain into three recurrent timeslots of fixed length, and then sequentially selects two sensing electrodes 20 at a time to obtain three time-multiplexed differential voltage signals $\Phi_{AB}$, $\Phi_{BC}$, $\Phi_{CA}$. In synchronization with the system clock 50, the microprocessor 80 selects the pair of sensing electrodes 20 according to a designated sampling frequency which determines the multiplexing timeslot length. For example, if the sampling frequency is 256 Hz, then the multiplexing timeslot length is about 3.9 ms.

The multiplexed signals $\Phi_{AB}$, $\Phi_{BC}$, $\Phi_{CA}$ are connected to the differential amplifiers 91 which amplify the differential voltage signals while providing common mode rejection. The amplified differential voltage signals are then connected to the analog filters 92, which include at least anti-aliasing low pass filters whose cut-off frequency corresponds to the highest frequency component of interest in subcutaneous ECG signals, e.g., 128 Hz. In addition, the analog filters 92 also include high pass filters with sufficiently low corner frequency, e.g., 0.5 Hz, to remove the DC offset component. Preferably, the analog filters 92 also include the 50 Hz or 60 Hz notch filters that remove the power-line interference.

Through the analog-to-digital converter (ADC) 93, the amplified and analog-filtered differential voltage signals are then converted to digital signals according to predefined or user-programmable sampling frequency, e.g., 128 Hz, 256 Hz, 512 Hz, etc. The converted digital signals are then further processed through digital filters 94 whose filter characteristics (e.g., filter type, order, gain, corner frequencies, etc.) are user-programmable. By adjusting the digital filter 94 characteristics, a user may optimize the signal quality for specific applications. For example, for reliable beat detection, a T wave may be attenuated to avoid T wave over-sensing.

Thus, the electrocardiogram (ECG) sensing unit 97, or the front-end of the cardiac device 100, converts the analog voltage input from three sensing electrodes 20 $\Phi_A$, $\Phi_B$ and $\Phi_c$ to three channels 6 of time-multiplexed digital subcutaneous ECG signals $U_{AB}$, $U_{BC}$ and $U_{CA}$ which represents a first step $S_1$ in this embodiment of the method according to the present invention. In a preferred embodiment, the gains and filter settings for all three channels 6 in the front-end are the same.

Figure 4:
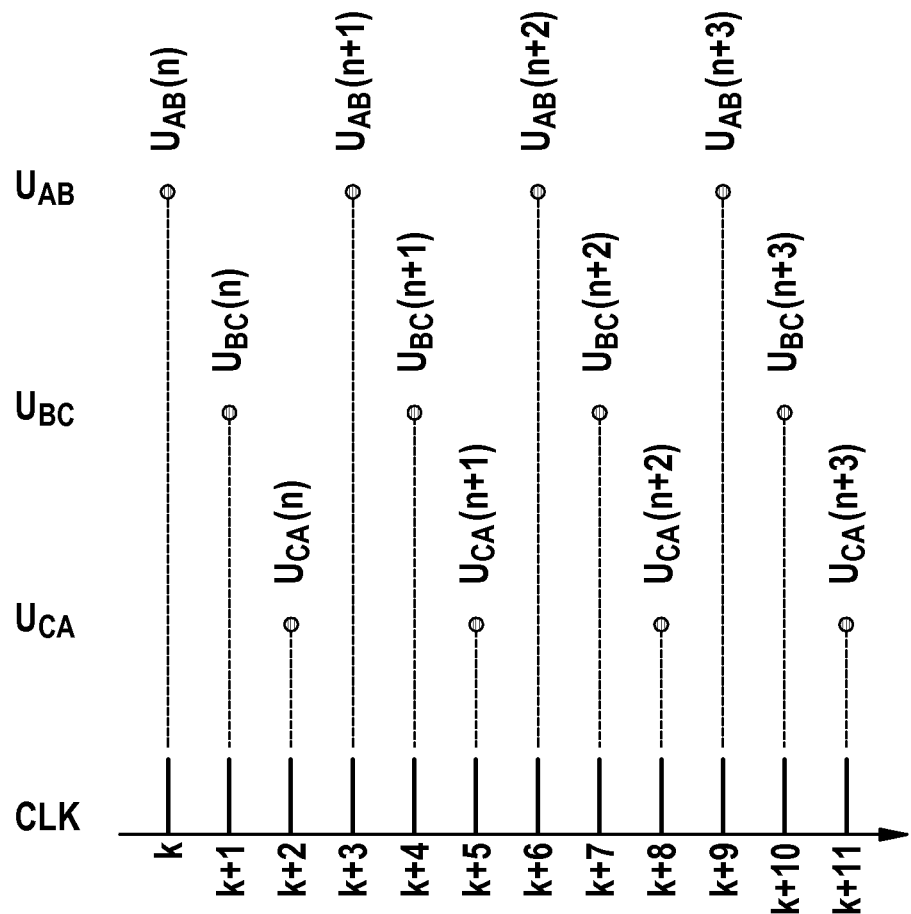
FIG. 4 shows a schematic drawing of multiplexing three-channel subcutaneous signals in synchronization with the sampling clock.

FIG. 4 shows a schematic drawing of multiplexing three-channel 6 subcutaneous signals in synchronization with the sampling clock 50. At the time slot k, the multiplexer 90 controls the generation of one sample digital output $U_{AB}(n)$ representing the differential voltage in lead AB measured at the time slot k, wherein n is the sample index. At the next time slot k+1, the multiplexer 90 controls the generation of one sample digital output $U_{BC}(n)$ representing the differential voltage in lead BC measured at the time slot k+1, wherein the sample index n remains unchanged. Then, at the next time slot k+2, the multiplexer 90 controls the generation of one sample digital output $U_{CA}(n)$ representing the differential voltage in lead CA measured at the time slot k+2, wherein the sample index n is still unchanged. Then, at the next time slot k+3, the multiplexer controls the generation of one sample digital output $U_{AB}(n+1)$ representing the differential voltage in lead AB measured at the time slot k+4, wherein the sample index is increased to n+1. Following the similar steps, the multiplexer 90 sequentially controls the generation of the sample output $U_{BC}(n+1)$, $U_{CA}(n+1)$, $U_{AB}(n+2)$, $U_{BC}(n+2)$, $U_{CA}(n+2)$, $U_{AB}(n+3)$, $U_{BC}(n+3)$, $U_{CA}(n+3)$ in the following time slots, and the process repeats. As a result, for each specific sample index, there is one digital sample in each of the three output channels 6. However, these three digital samples represent the differential voltages in respective leads that are measured at three different time slots.

Figure 5:
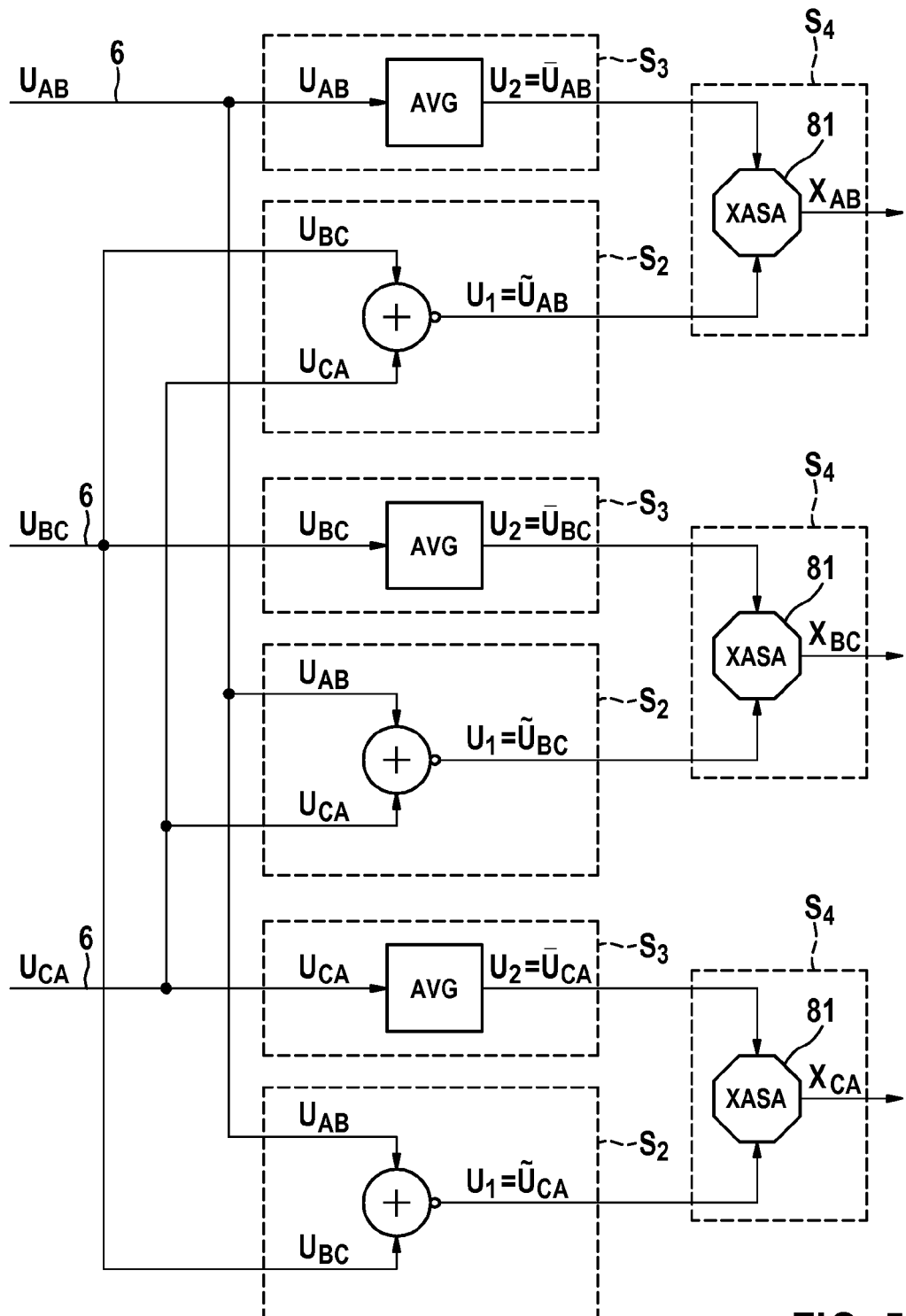
FIG. 5 shows a block diagram of generating three composite signals X that represent XASA signals $X_{AB}$, $X_{BC}$, $X_{CA}$ from three multiplexed differential voltage signals $U_{AB}$, $U_{BC}$, $U_{CA}$.

FIG. 5 shows a block diagram of generating three composite signals X that represent XASA signals $X_{AB}$, $X_{BC}$, $X_{CA}$ from three multiplexed differential voltage signals $U_{AB}$, $U_{BC}$, $U_{CA}$.

At an instant in time, cardiac electrical activity can be represented as a 3D dipolar vector, which is projected onto the 3 sensing channels 6. Therefore, $\Phi_{BC}$ measures the far-field projection of the cardiac vector along the BC axis, $\Phi_{CA}$ measures the far-field projection of the cardiac vector along the CA axis, and $\Phi_{AB}$ measures the far-field projection of the cardiac vector along the AB axis. According to the principles of vector arithmetic, at a time t, $\Phi_{AB}(t)=-(\Phi_{BC}(t)+\Phi_{CA}(t))$, $\Phi_{BC}(t)=-(\Phi_{AB}(t)+\Phi_{CA}(t))$, $\Phi_{CA}(t)=-(\Phi_{AB}(t)+\Phi_{BC}(t))$. Because the gains and filter settings for all three channels 6 in the front-end are the same, the same arithmetic relationship would also hold true for the three digital signals had the data been sampled at the same time, that is, at any time instant t, $U_{AB}(t)=-(U_{BC}(t)+U_{CA}(t))$, $U_{BC}(t)=-(U_{AB}(t)+U_{CA}(t))$, $U_{CA}(t)=-(U_{AB}(t)+U_{BC}(t))$.

However, because $U_{AB}$, $U_{BC}$, and $U_{CA}$ are time-multiplexed, for each specific sample index n, $U_{AB}(n)$, $U_{BC}(n)$, and $U_{CA}(n)$ are sampled at three adjacent, rather than the same, time slots. Therefore, $-(U_{BC}(n)+U_{CA}(n))$ is only an approximate of $U_{AB}(n)$, $-(U_{AB}(n)+U_{CA}(n))$ is only an approximate of $U_{BC}(n)$, and $-(U_{AB}(n)+U_{BC}(n))$ is only an approximate of $U_{CA}(n)$. In this embodiment of the present invention, first estimates $U_1$ from each of the three pairs of input signals are given with $U_{AB}(n)$, $U_{BC}(n)$ and $U_{CA}(n)$ for each specific sample index n, wherein $U_{AB}(n)$, $U_{BC}(n)$ and $U_{CA}(n)$ are generated within the second step S2 of the method according to the present invention.

Expressed in other words, within the second step $S_2$ of the method according to the embodiment of the present invention shown in FIG. 5, the differential voltage signals $U_{BC}$ and $U_{CA}$ are summed and then inverted to generate the signal $\tilde{U}_{AB}$, which is a first estimate $U_1$ of the signal $U_{AB}$. Similarly, $U_{AB}$ and $U_{CA}$ are summed and then inverted to generate the signal $\tilde{U}_{BC}$, which is a first estimate $U_1$ of the signal $U_{BC}$. Likewise, $U_{AB}$ and $U_{BC}$ are summed and then inverted to generate the signal $\tilde{U}_{CA}$, which provides a first estimate $U_1$ of the signal $U_{CA}$.

Furthermore, within the third step $S_3$ of the method according to the embodiment of the present invention shown in FIG. 5, the signals $U_{AB}$, $U_{BC}$ and $U_{CA}$ are further processed through moving average filters to generate the signals $\overline{U}_{AB}$, $\overline{U}_{BC}$ and $\overline{U}_{CA}$ as second estimates $U_2$. Expressed in other words, in this embodiment, the signals $U_{AB}$ are further processed through a moving average filter to generate the signal $\overline{U}_{AB}$, which is a second estimate $U_2$ of the signal $U_{AB}$. Similarly, $U_{BC}$ is further processed through a moving average filter to generate the signal $\overline{U}_{BC}$, which is a second estimate $U_2$ of the signal $U_{BC}$, and $U_{CA}$ is further processed through a moving average filter to generate the signal $\overline{U}_{CA}$, which is a second estimate $U_2$ of the signal $U_{CA}$.

In another embodiment of the present invention, the signals $U_{AB}$, $U_{BC}$ and $U_{CA}$ may directly be taken as second estimates $U_2$ for the subcutaneous ECG signal input. In such an embodiment, the signals $U_{AB}$, $U_{BC}$ and $U_{CA}$, as well as the signals $\tilde{U}_{AB}$, $\tilde{U}_{BC}$ and $\tilde{U}_{CA}$, are processed through further processing units 81, which are realized as so called XASA (Cross-check and Adjustment of Signal Amplitude)-units 81, within the fourth step $S_4$ of the method according to the present invention. Expressed in other words, according to such an embodiment of the present invention, the signals $U_{AB}$ and $\tilde{U}_{AB}$ are processed through a first further processing unit 81 within the fourth step $S_4$ of the method according to the present invention. This first further processing unit 81 is a first XASA-unit 81 which is designed to generate the composite signal $X_{AB}$. Similarly, $U_{BC}$ and $\tilde{U}_{BC}$ are processed through a second further processing unit 81, which is a second XASA-unit 81 to generate the composite signal $X_{BC}$, and $U_{CA}$ and $\tilde{U}_{CA}$ are processed through a third further processing unit 81, which is a third XASA-unit 81 to generate the composite signal $X_{CA}$.

In the embodiment of the present invention shown in FIG. 5, the processing of the signals $\overline{U}_{AB}$, $\overline{U}_{BC}$ and $\overline{U}_{CA}$ and the signals $\tilde{U}_{AB}$, $\tilde{U}_{BC}$ and $\tilde{U}_{CA}$ is also executed by further processing units 81 or XASA-units 81. In this embodiment, the further processing units 81 or the XASA-units 81 are exemplarily realized within the microprocessor 80 (not shown). In other embodiments of the present invention, further processing units 81 or XASA-units 81 may be realized as autonomous units which work isolated from other components of the cardiac device 100.

In FIG. 5, the signals $\tilde{U}_{AB}$, $\tilde{U}_{BC}$ and $\tilde{U}_{CA}$ are used as first estimates $U_1$, while the signals $\overline{U}_{AB}$, $\overline{U}_{BC}$ and $\overline{U}_{CA}$ are used as second estimates $U_2$. As shown in FIG. 5, the composite signal $X_{AB}$ from the first XASA-unit 81 is then obtained from $\tilde{U}_{AB}$ and $\overline{U}_{AB}$, which are two different estimates of $U_{AB}$. Likewise, the composite signal $X_{BC}$ from the second XASA-unit 81 is obtained from $\tilde{U}_{BC}$ and $\overline{U}_{BC}$, which are two different estimates of $U_{BC}$, and the composite signal $X_{CA}$ from the third XASA-unit 81 is obtained from $\tilde{U}_{CA}$ and $\overline{U}_{CA}$, which are two different estimates of $U_{CA}$.

The benefit of using moving average filters is to better align the second estimated signals to the first estimated signals, so to better align the second estimates $U_2$ to the first estimates $U_1$.

Referring back to FIG. 4, $U_{BC}(n)$ is sampled at the time slot k+1, and $U_{CA}(n)$ is sampled at the time slot k+2. Their combination $-(U_{BC}(n)+U_{CA}(n))$ yields a first estimate $U_1$ of $U_{AB}$ had it been sampled between the time slots k+1 and k+2. Meanwhile, the average of $U_{AB}(n)$ and $U_{AB}(n+1)$ provides a second estimate $U_2$ of $U_{AB}$ had it been sampled between the same time slots k+1 and k+2. Similarly, $U_{AB}(n+1)$ is sampled at the time slot k+3, and $U_{BC}(n+1)$ is sampled at the time slot k+4. Their combination $-(U_{AB}(n+1)+U_{BC}(n+1))$ yields a first estimate $U_1$ of $U_{CA}$ had it been sampled between the time slots k+3 and k+4. Meanwhile, the average of $U_{CA}(n)$ and $U_{CA}(n+1)$ provides a second estimate $U_2$ of $U_{CA}$ had it been sampled between the same time slots k+3 and k+4. On the other hand, note that $U_{AB}(n+1)$ is sampled at the time slot k+3, and $U_{CA}(n+1)$ is sampled at the time slot k+5. Their combination $U_{AB}(n+1)+U_{CA}(n+1)$ yields a first estimate $U_1$ of $U_{BC}$ sampled at the time slots k+4, which is exactly $U_{BC}(n+1)$. In this case, it is not necessary to apply a moving average to obtain a second estimate $U_2$ of $U_{BC}$, because $U_{BC}$ is already aligned with $U_{AB}+U_{CA}$. Alternatively, we can still apply a moving average filter to generate a second estimate $U_2$ of $U_{BC}$ without changing its alignment with $U+U_{CA}$. For example, $U_{BC}(n+1)$ can be estimated as the average of its two neighboring samples, i.e., $(U_{BC}(n)+U_{BC}(n+2))/2$, or the weighted average of three adjacent samples, i.e., $(U_{BC}(n)+2U_{BC}(n+1)+U_{BC}(n+2))/4$, etc.

Figure 6:
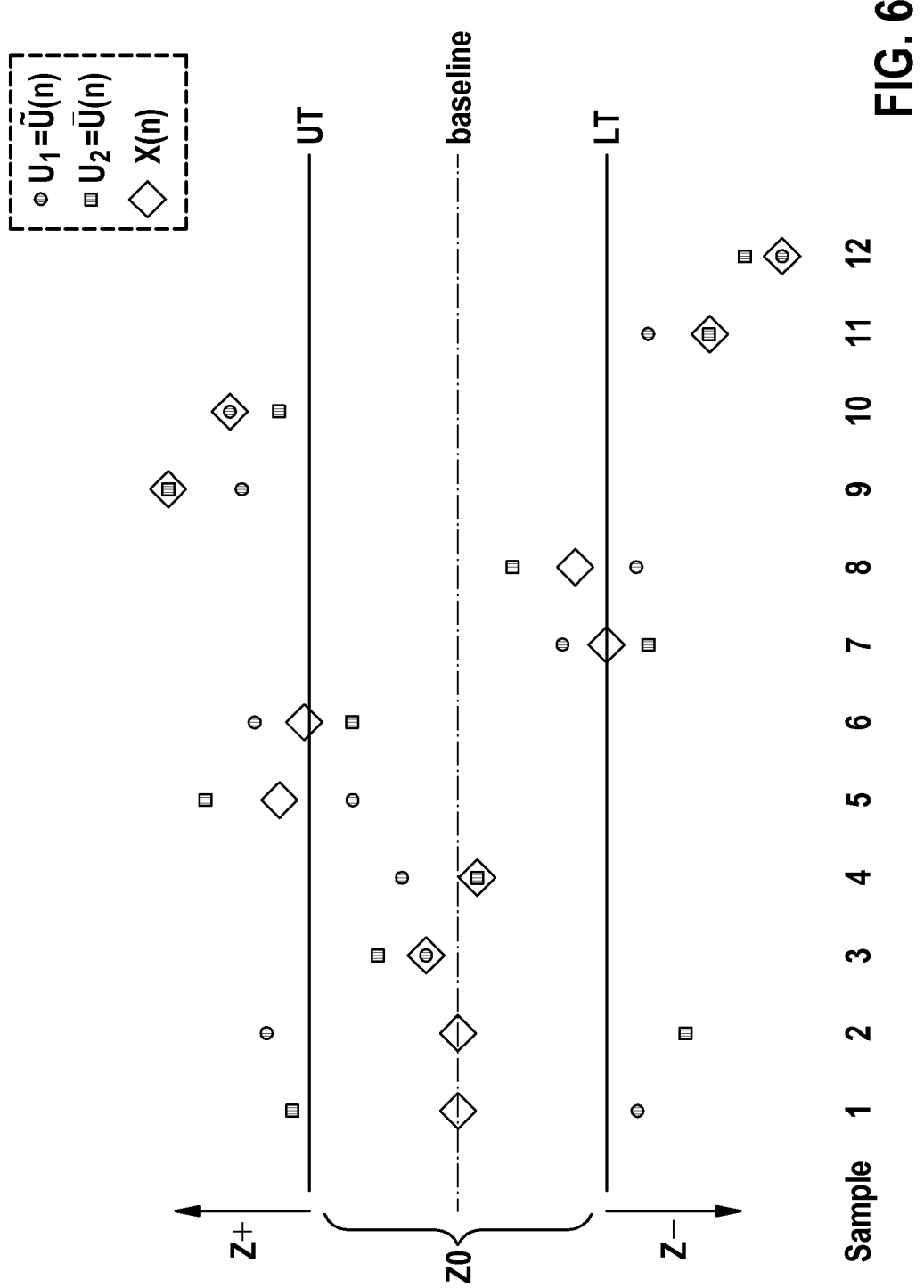
FIG. 6 illustrates the concept of three zones and the logical operation of a XASA algorithm performed by XASA-units in order to obtain composite signals X.

FIG. 6 illustrates the concept of three zones and the logical operation of an XASA algorithm performed by XASA-units 81 in order to obtain composite signals X. The XASA-units 81 continuously process two input signals, the first and second estimates $U_1=\tilde{U}$ and $U_2=\overline{U}$, to generate composite signals X. To implement the XASA function, the signal space is divided into three non-overlapping zones: a positive zone Z+, a null zone Z0, and a negative zone Z−. The three zones Z+, Z0, Z− are separated by two thresholds: an upper threshold UT, and a lower threshold LT. The positive zone Z+ refers to the subspace that is above the upper threshold UT, the negative zone Z− refers to the subspace that is below the lower threshold LT, and the null zone Z0 refers to the subspace that is bounded between the upper and the lower threshold UT and LT. Preferably, the upper and the lower threshold UT and LT are symmetric around the signal baseline, and their values are adaptive to the signal amplitude of the respective processing channel 6. In one embodiment, the upper and the lower threshold UT and LT are predefined by the user based on an evaluation of the signal amplitude in the processing channel 6. Yet according to another embodiment, the upper threshold UT and the lower threshold LT are automatically adjusted based on the moving average of the peak absolute amplitude of the previous QRS complexes that are detected in the processing channel 6. For example, a XASA-unit 81 retains the peak absolute amplitudes of the last four QRS complexes p1, p2, p3, p4 that are respectively detected in the composite signals X which are outputted by the XASA-unit 81, and calculates their average AvgPk=(p1+p2+p3+p4)/4. Then the upper threshold UT and the lower threshold LT are set to a predefined fraction of AvgPk. For example, UT may be set to UT=−LT=AvgPk/4, or may be set to UT=−LT=AvgPk/8. After each detection of a beat in the processing channel 6, the peak absolute amplitude of the new QRS complex is measured. Then the AvgPk is recalculated, and the upper threshold UT and the lower threshold LT are updated accordingly. Conceptually, the signal is in a positive phase if its samples are in the positive zone Z+, or the signal is in a negative phase if its samples are in the negative zone Z−, or the signal is near the baseline if its samples are in the null zone Z0.

Figure 7:
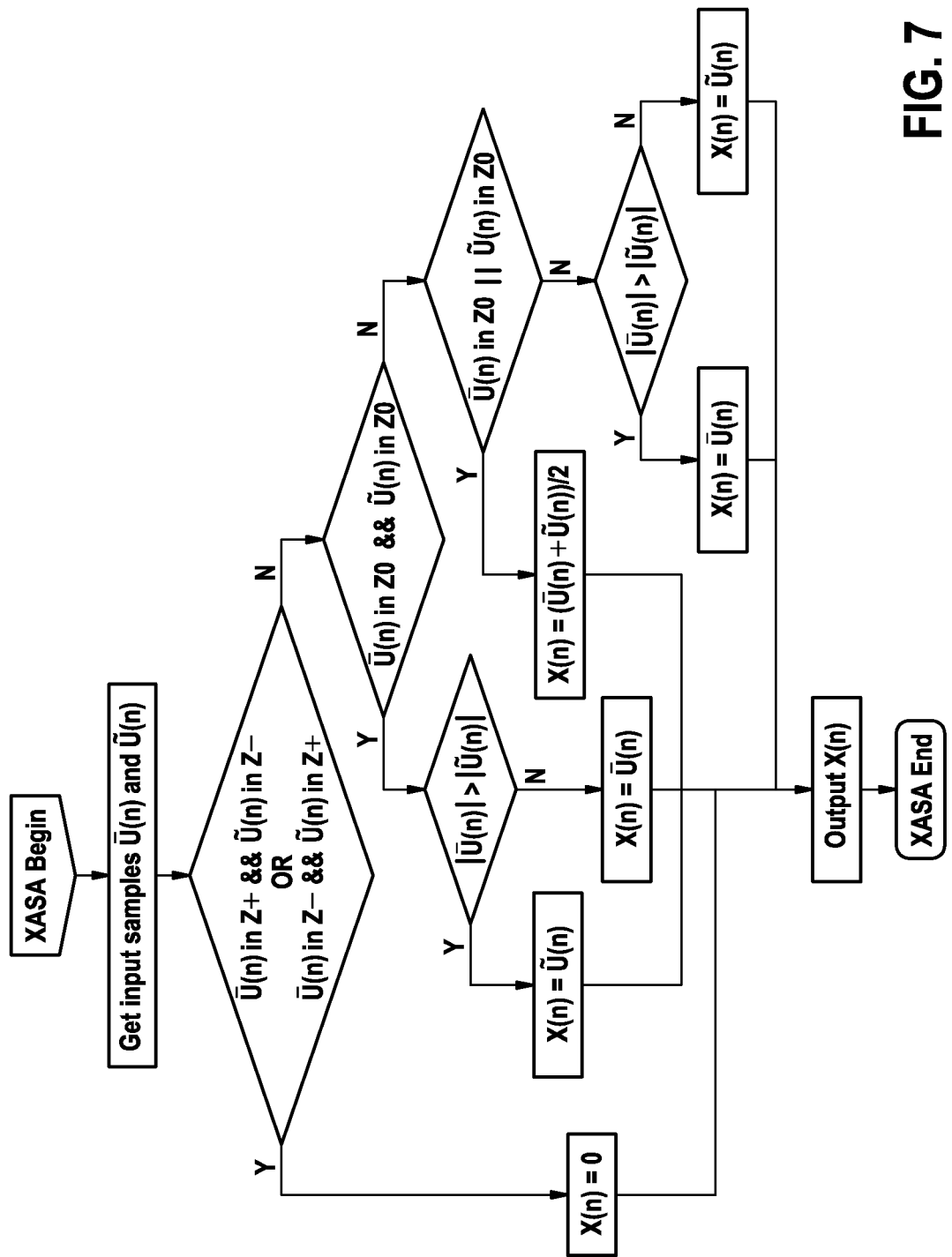
FIG. 7 shows a flowchart diagram that illustrates the implementation of the XASA function.

FIG. 7 shows a flowchart diagram that illustrates the implementation of the XASA function. For each sample index n, an XASA-unit 81 gets the pair of input samples $U_1=\tilde{U}(n)$ and $U_2=\overline{U}(n)$. Then the XASA-unit 81 performs a series of logical checks to determine the composite signal or output sample X(n) based on how $\tilde{U}(n)$ and $\overline{U}(n)$ are distributed in the three zones (Z+, Z0, Z−). There are a total of four possible conditions:

In the first condition, one sample is in Z+ and the other sample is in Z−:

$$(\tilde{U}(n)>UT) \text{ AND } (\overline{U}(n)<LT) \text{ OR } (\tilde{U}(n)<LT) \text{ AND } (\overline{U}(n)>UT)$$

Then the composite signal or output sample X(n) is set to 0. Expressed in other words, a composite signal X(n)=0 is generated if the corresponding first estimate $\tilde{U}(n)$ is lower than the lower threshold LT and the corresponding second estimate $\overline{U}(n)$ is greater than the upper threshold UT, or if the corresponding first estimate $\tilde{U}(n)$ is greater than the upper threshold UT and the corresponding second estimate $\overline{U}(n)$ is lower than the lower threshold LT. This condition implies that two different estimates of the sample amplitude $\tilde{U}(n)$ and $\overline{U}(n)$ have opposite phases. This large discrepancy suggests possible noise interference in the input signals.

In the second condition, both samples are in Z0:

$$(LT \leq \overline{U}(n) \leq UT) \text{ AND } (LT \leq \tilde{U}(n) \leq UT)$$

Then the composite signal or output sample X(n) is set to $\tilde{U}(n)$ if $|\overline{U}(n)|>|\tilde{U}(n)|$, or is set to $\overline{U}(n)$ if $|\overline{U}(n)| \leq |\tilde{U}(n)|$. Expressed in other words, if a first and second estimate $\tilde{U}(n)$, $\overline{U}(n)$ are both greater than or equal to the lower threshold LT and both lower than or equal to the upper threshold UT, a corresponding composite signal $X(n)=\tilde{U}(n)$ is generated if the absolute value of the corresponding second estimate $\overline{U}(n)$ is greater than the absolute value of the corresponding first estimate $\tilde{U}(n)$, or a corresponding composite signal $X(n)=\overline{U}(n)$ is generated if the absolute value of the corresponding first estimate $\tilde{U}(n)$ is greater than or equal to the absolute value of the corresponding second estimate $\overline{U}(n)$. This condition implies that both estimates of the sample amplitude $\tilde{U}(n)$ and $\overline{U}(n)$ are near the signal baseline, so the one that is closer to the signal baseline (i.e., the one with the smaller absolute amplitude) is chosen as the output amplitude.

In the third condition, only one sample is in Z0 but the other sample is in Z+ or Z−:

$$(LT \leq \overline{U}(n) \leq UT) \text{ AND } (\tilde{U}(n)>UT \text{ OR } \tilde{U}(n)<LT) \text{ OR }$$
$$(LT \leq \tilde{U}(n) \leq UT) \text{ AND } (\overline{U}(n)>UT \text{ OR } \overline{U}(n)<LT)$$

Then the composite signal or output sample X(n) is set to $(\tilde{U}(n)+\overline{U}(n))/2$. Expressed in other words, a composite signal X(n) equal to the arithmetic mean of a corresponding first and second estimate $\tilde{U}(n)$, $\overline{U}(n)$ is generated if the corresponding second estimate $\overline{U}(n)$ is greater than or equal to the lower threshold LT and lower than or equal to the upper threshold UT, while the corresponding first estimate $\tilde{U}(n)$ is either greater than the upper threshold UT or lower than the lower threshold LT, or if a corresponding first estimate $\tilde{U}(n)$ is greater than or equal to the lower threshold LT and lower than or equal to the upper threshold UT, while the corresponding second estimate $\overline{U}(n)$ is either greater than the upper threshold UT or lower than the lower threshold LT. This condition implies that there is a modest discrepancy between the two estimates of the sample amplitudes $\tilde{U}(n)$ and $\overline{U}(n)$, thus their average value is chosen as the output amplitude.

In the fourth condition, both samples are in Z+ or both samples are in Z−:

$$(\overline{U}(n)>UT \text{ AND } \tilde{U}(n)>UT) \text{ OR } (\overline{U}(n)<LT \text{ AND } \tilde{U}(n)<LT)$$

Then the output sample X(n) is set to $\overline{U}(n)$ if $|\overline{U}(n)|>|\tilde{U}(n)|$, or is set to $\tilde{U}(n)$ if $|\overline{U}(n)| \leq |\tilde{U}(n)|$. Expressed in other words, if a first and second estimate $\tilde{U}(n)$ and $\overline{U}(n)$ are both greater than the upper threshold UT or both lower than the lower threshold LT, a corresponding composite signal $X(n)=\overline{U}(n)$ is generated if the absolute value of the corresponding second estimate $\overline{U}(n)$ is greater than the absolute value of the corresponding first estimate $\tilde{U}(n)$, or a corresponding composite signal $X(n)=\tilde{U}(n)$ is generated if the absolute value of the corresponding first estimate $\tilde{U}(n)$ is greater than or equal to the absolute value of the corresponding second estimate $\overline{U}(n)$. This condition implies that both estimates of the sample amplitudes $\tilde{U}(n)$ and $\overline{U}(n)$ have a consistent phase, suggesting it belongs to a signal component, so the one that has larger absolute amplitude is chosen as the output amplitude.

The operation of the XASA function could be further illustrated by the example shown in FIG. 6. The example shows twelve pairs of input samples $\tilde{U}(n)$ and $\overline{U}(n)$, as well as the corresponding composite signals or output samples X(n). For the 1st sample pair, $\overline{U}(1)$ is in Z+ and $\tilde{U}(1)$ is in Z−, thus X(1)=0. For the 2nd sample pair, $\tilde{U}(2)$ is in Z− and $\tilde{U}(2)$ is in Z+, thus X(2)=0. In the 3rd sample pair, $\tilde{U}(3)$ and $\overline{U}(3)$ are both in Z0, and $X(3)=\tilde{U}(3)$ because $|\overline{U}(3)|>|\tilde{U}(3)|$. In the 4th sample pair, $\tilde{U}(4)$ and $\tilde{U}(4)$ are also both in Z0, and $X(4)=\overline{U}(4)$ because $|\overline{U}(4)|<|\tilde{U}(4)|$. For the 5th and the 6th sample pairs, one sample is in Z+ and the other sample is in Z0, so $X(5)=(\tilde{U}(5)+\overline{U}(5))/2$ and $X(6)=(\tilde{U}(6)+\overline{U}(6))/2$. For the 7th and the 8th sample pairs, one sample is in Z− and the other sample is in Z0, so $X(7)=(\tilde{U}(7)+\overline{U}(7))/2$ and $X(8)=(\tilde{U}(8)+\overline{U}(8))/2$. For the last four sample pairs (9th through 12th), either both samples are in Z+ or both samples are in Z−, so the one with larger absolute amplitude is chosen as output, i.e., $X(9)=\overline{U}(9)$, $X(10)=\tilde{U}(10)$, $X(11)=\overline{U}(11)$, $X(12)=\tilde{U}(12)$.

Normal subcutaneous ECG signals generally have distinctive signal components, such as, for example, a P wave, a QRS complex and a T wave. With a sufficiently high sampling frequency, each of these signal components can be represented by multiple samples in a digitized signal. For example, a QRS complex with 100 ms duration can be represented by 25-26 samples at the sampling frequency 256 Hz. Consequently, the morphology of the signal component is rarely affected by the input multiplexing. For example, the QRS complex morphology in a channel 6 $U_{AB}$ is almost the same no matter the signal is sampled at the time slots k, k+3, k+6, k+9, etc, or sampled at the time slots k+1, k+4, k+7, k+10, etc, or sampled at the time slots k+2, k+5, k+8, k+11, etc.

In contrast, many noises, such as, for example, myopotentials, EMI, electronic thermal noise, and many other electrical activities originating from outside the heart, have much higher frequency components. These noise components are usually added to the subcutaneous ECG and shown as random impulses with relatively short durations. As a result, these noise components are more sensitive to input multiplexing. For example, assume the sampling frequency is 256 Hz. If a noise impulse has a duration that is shorter than 4 ms, it is very likely that the noise impulse is sampled at one channel 6 at a certain time slot, but not sampled at the other two channels 6 due to multiplexing. Similarly, at the sampling frequency 256 Hz, a noise impulse with a duration shorter than 8 ms may be sampled by two channels 6 at two adjacent time slots, but not detected in the third channel 6. Even if the noise duration is longer and the noise component is sampled in all three channels 6, the noise component sampled in one channel 6 may have a very different morphology than the one estimated from the other two channels 6, because the noise amplitude may vary significantly from one time slot to the next time slot.

Referring to FIG. 7, because the signal component is not sensitive to multiplexing, whereas the noise component is more sensitive to multiplexing, an XASA-unit 81 can preserve the signal component while suppressing the noise component. For example, assume the subcutaneous ECG in a channel 6 U shows a QRS complex at the sample index n. Then the signal component (sample amplitude of QRS waveform) is likely present in both its first estimate $\tilde{U}(n)$ and its second estimate $\overline{U}(n)$, and these two estimates likely have a similar sample amplitude with a same phase. Since the composite signal or output signal X(n) of an XASA-unit 81 equals to the input sample that has the larger absolute amplitude, the signal peak component (both amplitude and phase) is usually preserved. In contrast, assume the subcutaneous ECG in channel 6 U is contaminated by noise at the sample index n. Then it is very likely that the noise component is not consistently present in both estimates $\tilde{U}(n)$ and $\overline{U}(n)$. For example, the noise component may be absent in $\tilde{U}(n)$ and/or $\overline{U}(n)$, or has a reduced amplitude in $\tilde{U}(n)$ and/or $\overline{U}(n)$. Even if a noise component is present in both $\tilde{U}(n)$ and $\overline{U}(n)$, it is likely that $\tilde{U}(n)$ and $\overline{U}(n)$ have very different amplitudes and possibly have different phases. If $\tilde{U}(n)$ and $\overline{U}(n)$ are separated in Z+ and Z−, then the composite signal or output signal X(n) of an XASA-unit 81 is set to 0. If one input sample is in Z0 and the other sample is in Z+ or Z−, then the composite signal or output signal X(n) of an XASA-unit 81 will also be attenuated by taking the average of the two input samples. Therefore, by preserving the signal component while suppressing the noise component, the composite signals or output signals X(n) of an XASA-unit 81 XAB, XBC, and XCA have a much higher signal-to-noise ratio (SNR) than their counterparts UAB, UBC, and UCA.

According to this embodiment of the present invention, the beat detection algorithm is respectively applied to at least three composite signals or output signals XAB, XBC, and XCA of the XASA-units 81. One exemplary beat detection algorithm is the Auto-Sensing algorithm, which has been disclosed in U.S. Pat. No. 5,891,048. In brief, the Auto-Sensing algorithm applies a detection hold-off period after each peak detection, then automatically adjusts the sensing threshold, which is adaptive to the measured peak amplitude of the QRS complex and varies based on a predetermined time dependence. Therefore, for each composite signal or output signal X(n) of the XASA-units 81, the beat detection algorithm generates a series of sense markers for the respective specific channel 6. Within a sixth step $S_6$ (not shown) of the method according to a preferred embodiment of the present invention, the resulting three series of sense markers are provided to a vote unit for generating the final sense marker output as output signals. Specifically, if a QRS complex is detected in 2 out of 3 composite signals X(n) of the XASA-units 81 within a predefined time window (i.e., tolerance of difference in detection time), e.g., 50 ms, then a sense marker is generated for the final beat detection output. Otherwise, if, for example, only one of the three composite signals X(n) of the XASA-units 81 has a beat detection, then no sense marker is generated for the final beat detection output. According to another embodiment of the present invention, if and only if a QRS complex is detected in all 3 composite signals X(n) of the XASA-units 81 within a predefined time window (i.e., tolerance of difference in detection time), e.g., 50 ms, then a sense marker is generated for the final beat detection output. Yet according to a further embodiment of the present invention, if a QRS complex is detected in any one of the 3 composite signals X(n) of the XASA-units 81, then a sense marker is generated for the final beat detection output.

FIG. 8 shows an example of three channels 6 of time-multiplexed digital subcutaneous ECG signals $U_{AB}$, $U_{BC}$ and $U_{CA}$. Despite the filtering by the electrocardiogram (ECG) sensing unit 97 or the front-end circuit, the signals are contaminated by high frequency noise. The noise power is only slightly lower than the signal power, such that it is difficult to differentiate some true QRS complexes from noise deflections (see, for example, the marked dashed circles).

FIG. 9 shows the signals $\tilde{U}_{AB}$, $\tilde{U}_{BC}$, $\tilde{U}_{CA}$ that are estimated from the time-multiplexed differential signals $U_{AB}$, $U_{BC}$ and $U_{CA}$. Although, in general, the estimated signals $\tilde{U}_{AB}$, $\tilde{U}_{BC}$, $\tilde{U}_{CA}$ bear some similarity to the respective signals $U_{AB}$, $U_{BC}$ and $U_{CA}$, their morphological differences are also evident. Still, the estimated signals are contaminated by high frequency noise. The noise power is only slightly lower than the signal power, such that it is difficult to differentiate some true QRS complexes from noise deflections (see for example the marked dashed circles).

FIG. 10 shows the composite signals $X_{AB}$, $X_{BC}$, and $X_{CA}$ which are outputted by the XASA-units 81 and respectively constructed from the first estimated signals $\tilde{U}_{AB}$, $\tilde{U}_{BC}$, $\tilde{U}_{CA}$, and the second estimated signals $\overline{U}_{AB}$, $\overline{U}_{BC}$ and $\overline{U}_{CA}$. In addition, the final sense markers, as determined by the method according to one embodiment of the present invention as described above, are also shown. Clearly, for each channel 6, the signal components (QRS complexes) are preserved, whereas the noise components are substantially reduced. The spurious deflections observed in FIGS. 8-9 are either confirmed or rejected as QRS complexes.

In the foregoing embodiments, the described method according to the present invention discloses three XASA-units 81 that perform a specific XASA-algorithm on the inputted estimates $U_1$ and $U_2$, as described above. There also can be other embodiments of methods according to the present invention, in which other algorithms are applied on first and/or second estimates $U_1$ and/or $U_2$. For example, a method in which first and second estimates $U_1$ and $U_2$ are compared to just one threshold T or to four or more thresholds can also be according to the present invention. Furthermore, a first estimate $U_1$ does not necessarily need to be a differential signal and a second estimate $U_2$ must not be generated through moving average filters.

Figure 11B:
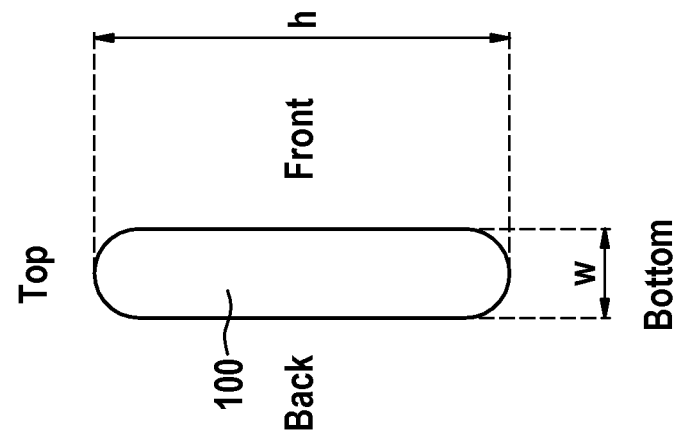
FIGS. 11A-B illustrate a first spiral shaped embodiment of the cardiac device according to the present invention.
Figure 11A:
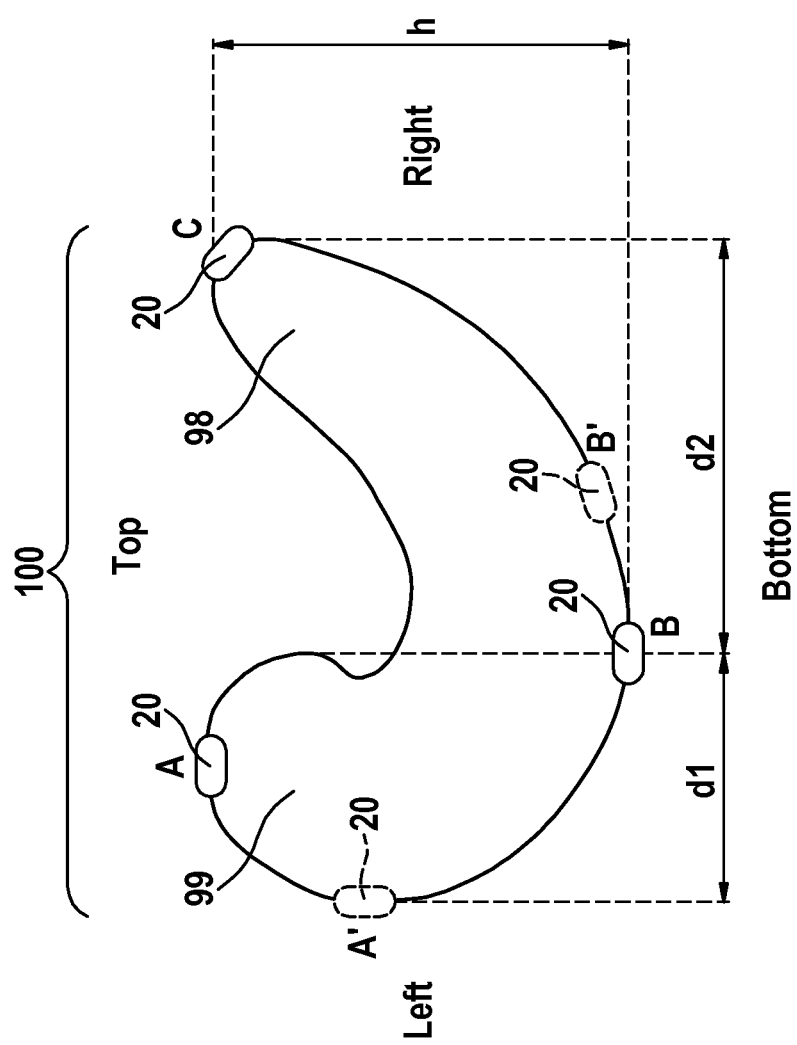

FIG. 11 illustrates a first spiral shaped embodiment of the cardiac device 100 according to the present invention. The front view of the cardiac device 100 in this embodiment is shown in FIG. 11A, and the side view of the cardiac device 100 in this embodiment is shown in FIG. 11B. As shown in FIG. 11, the front view of the cardiac device 100 has an asymmetric geometry that resembles a spiral shape. Specifically, the left side, which is the head 99 of the cardiac device 100, is wider than the right side, which is the tail 98 of the cardiac device 100.

Figure 12B:
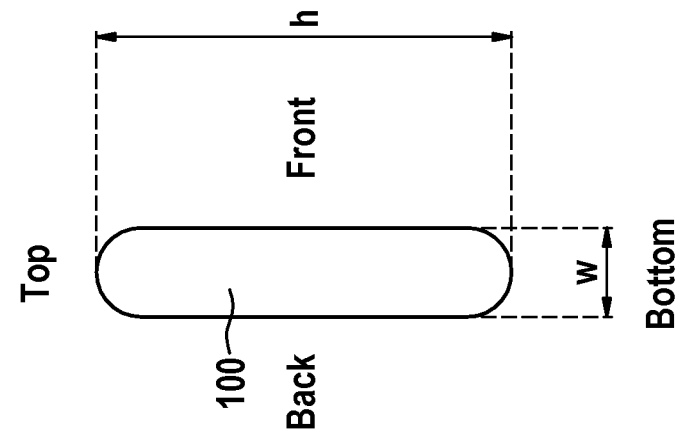
FIGS. 12A-B illustrate a second spiral shaped embodiment of the cardiac device according to the present invention.
Figure 12A:
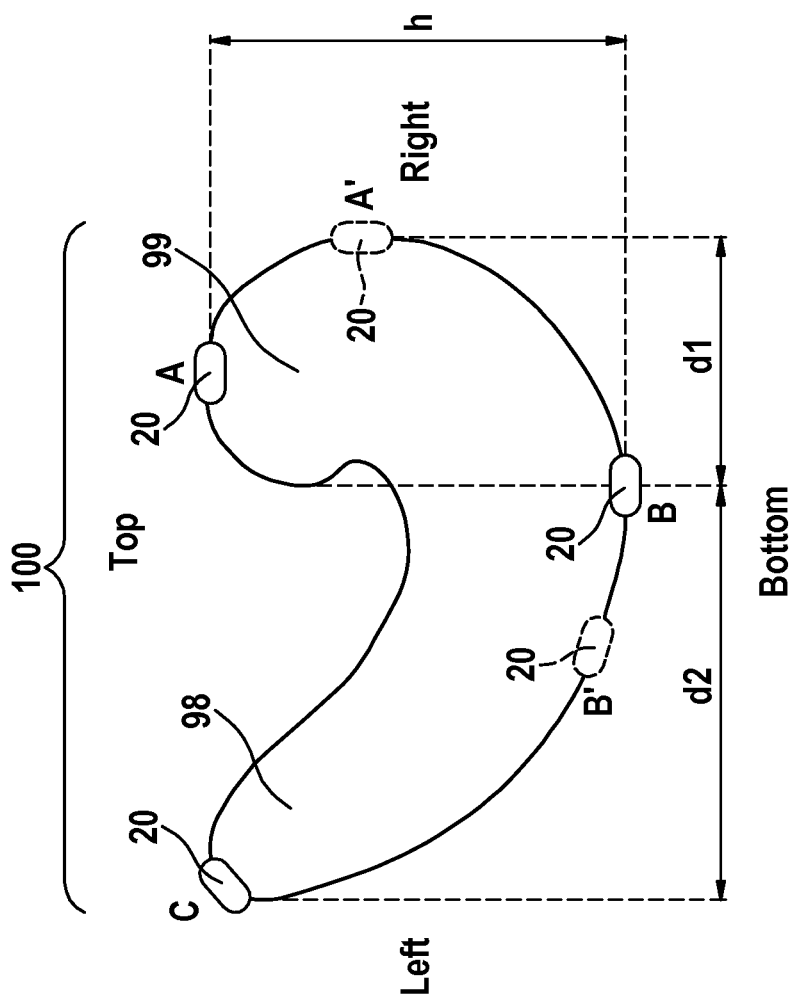

FIG. 12 illustrates a second spiral shaped embodiment of the cardiac device 100 according to the present invention. This second embodiment mirrors the one shown in FIG. 11 regarding the shape of the front view of the embodiment of the cardiac device 100. The front view of the cardiac device 100 in this embodiment is shown in FIG. 12A, and the side view of the cardiac device 100 in this embodiment is shown in FIG. 12B. Similarly, the front view of the cardiac device 100 has an asymmetric geometry that resembles a spiral shape. Specifically, the right side, which is the head 99 of the cardiac device 100 is wider than the left side, which is the tail 98 of the cardiac device 100.

In both spiral shaped embodiments of FIGS. 11-12, the cardiac device 100 features a rounded head 99 and a rounded tail 98. The bottom contour of the cardiac device 100 in both spiral shaped embodiments has a shape that approximates the Fibonacci spiral, and the top contour of the cardiac device 100 also follows a spiral shape except being rounded at the head 99 and tail 98. In both spiral shaped embodiments, the length $d_1$ of the head 99 of the cardiac device 100 is shorter than the length $d_2$ of the remaining segment, namely, the length $d_2$ of the tail 98. In the spiral shaped embodiments of the cardiac device 100, the two lengths $d_1$ and $d_2$ respectively have a mathematical relationship that approximates the golden ratio, that is, $(d_1+d_2)/d_2 \approx d_2/d_1$, wherein the golden ratio is $d_2/d_1 \approx (1+\sqrt{5})/2 \approx 1.6$, wherein in both embodiments the deviation from the value of 1.6 is smaller than 0.1. In both spiral shaped embodiments, the left-right length $(d_1+d_2)$ of the cardiac device 100 is between 2 cm and 6 cm. In the first spiral shaped embodiment of the present invention shown in FIG. 11, left-right length $(d_1+d_2)$ is equal to 5 cm. In the second spiral shaped embodiment of the present invention shown in FIG. 12, the left-right length $(d_1+d_2)$ is equal to 4 cm. In both spiral shaped embodiments of the invention, the top-bottom height h of the cardiac device 100 is between 1 cm and 3 cm, and the back-front thickness w of the cardiac device 100 is less than 1 cm. In the first spiral shaped embodiment of the cardiac device 100 shown in FIG. 11, the top-bottom height h is equal to 2.5 cm and the back-front thickness w of the cardiac device 100 is equal to 0.6 cm. In the second spiral shaped embodiment of the cardiac device 100 shown in FIG. 12 the top-bottom height h is equal to 2.8 cm and the back-front thickness w of the cardiac device 100 is equal to 0.75 cm.

In both embodiments of the present invention, three sensing electrodes 20 labeled A, B, and C, are respectively located in the top of the head 99 of the cardiac device 100 A, the bottom of the cardiac device 100 B, and the end of the tail 98 of the cardiac device 100 C. This positioning of the sensing electrodes 20 is only exemplary, and other positions are contemplated. A positioning of sensing electrodes 20 can differ from the one illustrated in FIGS. 11 and 12. For example, in another embodiment, one sensing electrode 20 may be positioned at the left edge of the cardiac device 100 A'. Yet according to another embodiment, one sensing electrode 20 B' may be positioned along the edge between the sensing electrodes 20 B and C according to specific geometric constraints, for example, to make the distance between the sensing electrodes 20 A and B' equal to the distance between sensing electrodes 20 B' and C, or to make the distance between the sensing electrodes 20 A' and B' equal to the distance between the sensing electrodes 20 B' and C, etc. Obviously, multiple sensing vectors can be formed by these spatially distributed sensing electrodes 20.

Figure 13B:
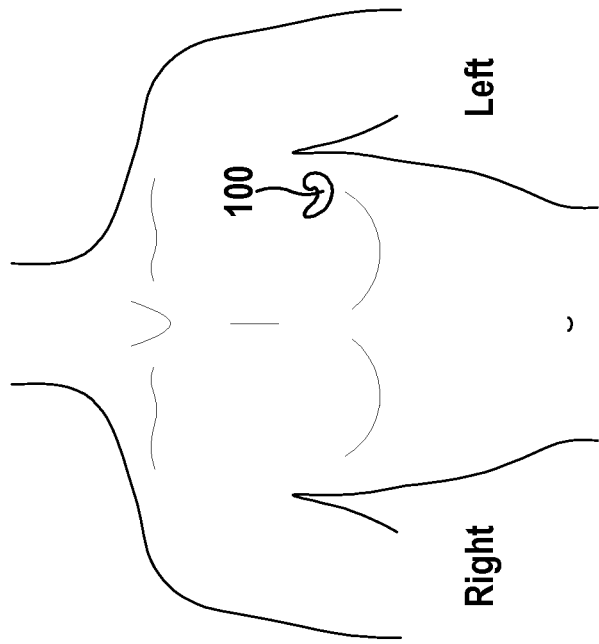
FIGS. 13A-B schematically illustrate two exemplary representative placements for the implantation of a spiral-shaped embodiment of a cardiac device in a human body.
Figure 13A:
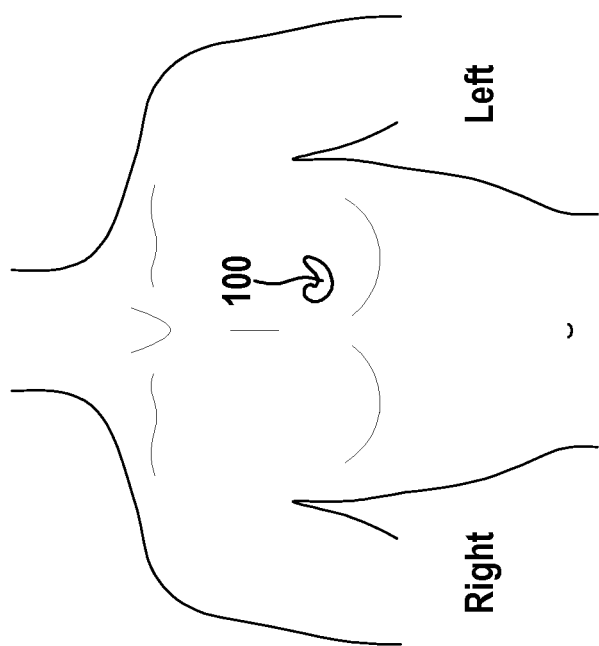

FIG. 13 schematically illustrates two exemplary representative placements for the implantation of a spiral-shaped embodiment of a cardiac device 100 in a human body. In FIG. 13A, the spiral shaped cardiac device 100 (shown in FIG. 11) is implanted in a subcutaneous pocket that is located just to the left side of the sternum. When viewed from the front, the thicker head 99 of the cardiac device 99 points to the sternum, and the thinner tail 98 of the cardiac device 100 points to the left side. In FIG. 13B, the spiral shaped cardiac device 100 (shown in FIG. 12) is implanted in a subcutaneous pocket that is created from the left anterior axillary line. When viewed from the front, the thicker head 99 of the cardiac device 100 points to the left side, and the thinner tail 98 of the cardiac device 100 points to the sternum. In both placements, the bottom of the cardiac device 100 sits in the pocket and the top of the cardiac device 100 points upward.

Figure 14A:
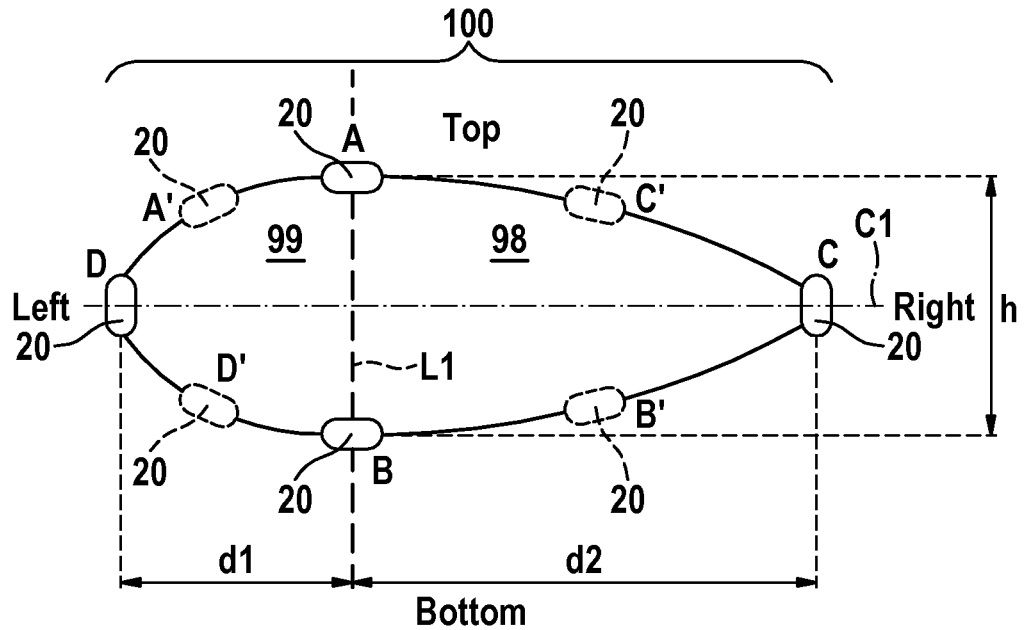
FIGS. 14A-C illustrate a first egg-oval shaped embodiment of the cardiac device according to the present invention.
Figure 14B:
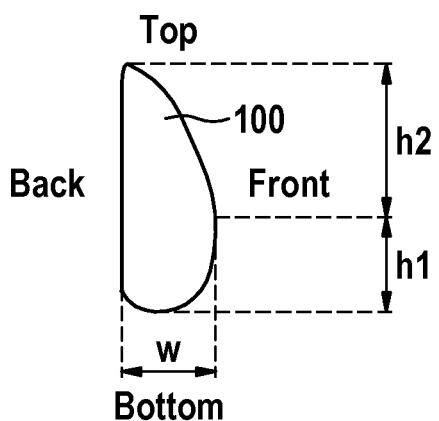
Figure 14C:
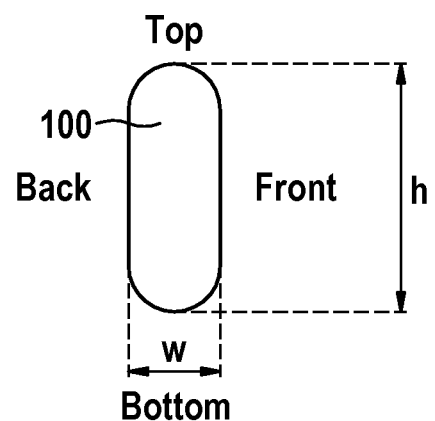

FIG. 14 illustrates a first egg-oval shaped embodiment of the cardiac device 100 according to the present invention. The front view of the cardiac device 100 in this embodiment is shown in FIG. 14A. Two possible embodiments regarding the side view of the cardiac device 100 are shown in FIG. 14B and in FIG. 14C. As shown in FIG. 14, the front view of the cardiac device 100 in this embodiment has a geometry that resembles an egg-oval shape. Specifically, the left side, or the head 99 of the cardiac device 100, is wider than the right side, or the tail 98 of the cardiac device 100. In this embodiment, the side view of the cardiac device 100 shows an asymmetric geometry that features a flat back surface and a spiral-curved front surface, that is according to the shape of the side view of the embodiment shown in FIG. 14B. In particular, viewed from the side in an upright position, the top of the cardiac device 100 is thinner and the bottom of the cardiac device 100 is thicker in this embodiment of the present invention. Alternatively, the side view of the cardiac device 100 may exemplarily also be designed to have a symmetric geometry. For example, in another embodiment, the cardiac device 100 may have the same thickness from top to bottom as shown in FIG. 14C.

Figure 15A:
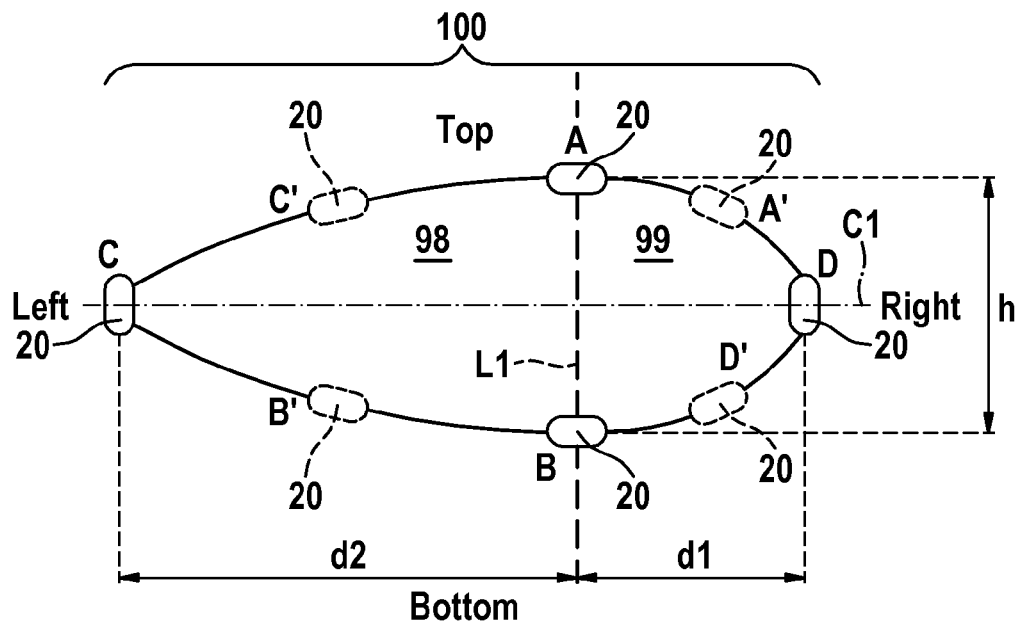
FIGS. 15A-C illustrate a second egg-oval shaped embodiment of the cardiac device according to the present invention.
Figure 15B:
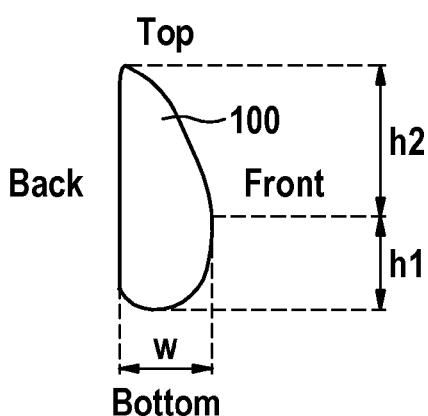
Figure 15C:
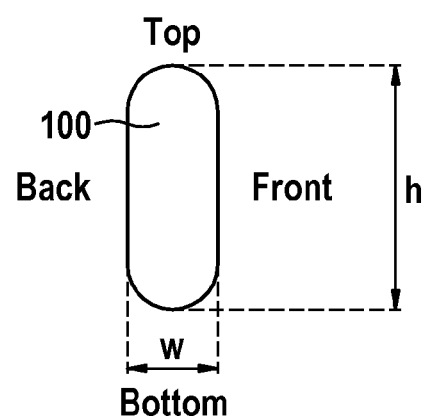

FIG. 15 illustrates a second egg-oval shaped embodiment of the cardiac device 100 according to the present invention. This second embodiment mirrors the one shown in FIG. 14, regarding the shape of the front view of the embodiment of the cardiac device 100. The front view of the cardiac device 100 in this embodiment is shown in FIG. 15A. Two possible embodiments of the side view of the cardiac device 100 are shown in FIG. 15B and in FIG. 15C. Similarly, the front view of the cardiac device 100 in this embodiment has a geometry that resembles an egg-oval shape. Specifically, the right side, or the head 99 of the cardiac device 100, is wider than the left side, or the tail 98 of the cardiac device 100. In the embodiment of the cardiac device 100 shown in FIG. 15, the side view of the cardiac device 100 has a symmetric shape that is according to the one shown in FIG. 15C. Expressed in other words, in this embodiment of the present invention, the side view of the cardiac device 100 has a symmetric geometry with the same thickness from top to bottom as shown in FIG. 15C.

Both embodiments of the cardiac device 100 according to the present invention as shown in FIG. 14 and FIG. 15 feature a rounded head 99 and a rounded tail 98. Expressed in other words, the outside contour of the front surface of both egg-oval shaped embodiments is rounded. The length $d_1$ of the head 99 of the cardiac device 100 is, in both embodiments, shorter than the length $d_2$ of the remaining segment, which is the tail 98 of the cardiac device 100. Furthermore, in both embodiments, the two lengths $d_1$ and $d_2$ have a mathematical relationship that is a close approximation of the golden ratio, that is, $(d_1+d_2)/d_2=d_2/d_1$, wherein $d_2/d_1=1.6$. While the first egg-oval shaped embodiment of the cardiac device 100 shown in FIG. 14 has an asymmetric geometry design when viewed from the side as shown in FIG. 14B, the second egg-oval shaped embodiment of the cardiac device 100 shown in FIG. 15 has a symmetric geometry design when viewed from the side as shown in FIG. 15C. For the side view of the first egg-oval shaped embodiment shown in FIG. 14, the height $h_1$ of the bottom part is shorter than the height $h_2$ of the top part of the cardiac device 100. Furthermore, in this embodiment, the heights $h_1$ and $h_2$ of the bottom and top sections have a mathematical relationship that also is a close approximation of the golden ratio, that is, $(h_1+h_2)/h_2=h_2/h_1$, wherein $h_2/h_1=1.6$. In both egg-oval shaped embodiments of the present invention, the left-right length $(d_1+d_2)$ of the cardiac device 100 is between 2 cm and 6 cm. The first egg-oval shaped embodiment shown in FIG. 14 exemplarily has a left-right length $(d_1+d_2)$ of 4 cm, while the second egg-oval shaped embodiment shown in FIG. 15 exemplarily has a left-right length $(d_1+d_2)$ of 5 cm. In both egg-oval shaped embodiments of the cardiac device 100, the top-bottom height $(h=h_1+h_2)$ of the cardiac device 100 is between 1 cm and 3 cm, and the back-front thickness w of the cardiac device 100 is less than 1 cm. The first egg-oval shaped embodiment of the cardiac device 100 shown in FIG. 14 exemplarily has a top-bottom height $(h=h_1+h_2)$ of 2 cm and a back-front thickness w of 0.8 cm. The second egg-oval shaped embodiment of the cardiac device 100 shown in FIG. 15 exemplarily has a top-bottom height h of 2.5 cm and a back-front thickness w of 0.9 cm. In both egg-oval shaped embodiments of the cardiac device 100, the front view of the cardiac device 100 shown in the FIGS. 14-15 is symmetric to a first centerline C1.

Furthermore, in both embodiments shown in FIGS. 14-15, four sensing electrodes 20 labeled A, B, C, and D are respectively located in the top of the cardiac device 100 A, in the bottom of the cardiac device B, in the tail 98 of the cardiac device 100 C, and in the head 98 of the cardiac device 100 D. This positioning of the sensing electrodes 20 is only exemplary. Other positions are also contemplated. A positioning of sensing electrodes 20 can differ from the one illustrated in FIGS. 14-15. For example, in other embodiments, a sensing electrode 20 A' may be positioned along the edge between the sensing electrodes 20 A and D, for example, with an equal distance to A and D. Yet in another embodiment, a sensing electrode 20 D' may be positioned along the edge between the sensing electrodes 20 D and B, for example, with an equal distance to D and B. Yet in further embodiments, a sensing electrode 20 B' may be positioned along the edge between the sensing electrodes 20 B and C, for example, with an equal distance to B and C. Yet in another embodiment, a sensing electrode 20 C' may be positioned along the edge between the sensing electrodes 20 C and A, for example, with an equal distance to C and A. Evidently, multiple sensing vectors can be formed by these spatially distributed sensing electrodes 20.

Expressed in other words, in both egg-oval shaped embodiments of the cardiac device 100 according to the present invention as shown in FIGS. 14-15, the cardiac device 100 comprises four external sensing electrodes 20, wherein two of the external sensing electrodes 20 are respectively located with the greatest distance possible to each other, in the tail 98 and the head 99 of the cardiac device 100, at the intersection points of the first centerline C1 with the circumference of the cardiac device 100 in the front view. In both egg-oval shaped embodiments of the cardiac device 100 as shown in the FIGS. 14-15, the other two of the external sensing electrodes 20 are located in the top and bottom of the cardiac device 100 in the front view, positioned at the intersection points of a line L1 with the circumference of the cardiac device 100, wherein in this embodiment, the line L1 is orthogonal to the first centerline C1. Moreover, in the second egg-oval shaped embodiment of the cardiac device 100 as shown in FIG. 15, the line L1 is furthermore crossing the center of gravity of the cardiac device 100.

Figure 16A:
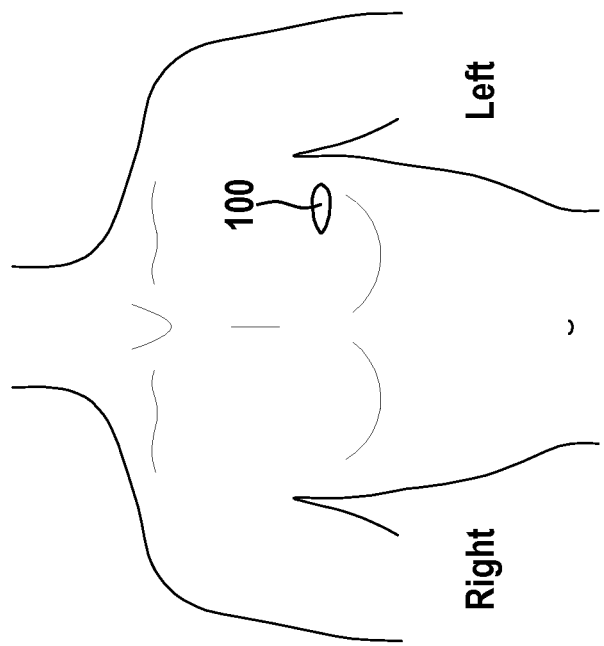
FIGS. 16A-B schematically illustrate two exemplary representative placements for the implantation of an egg-oval shaped cardiac device in a human body.
Figure 16B:
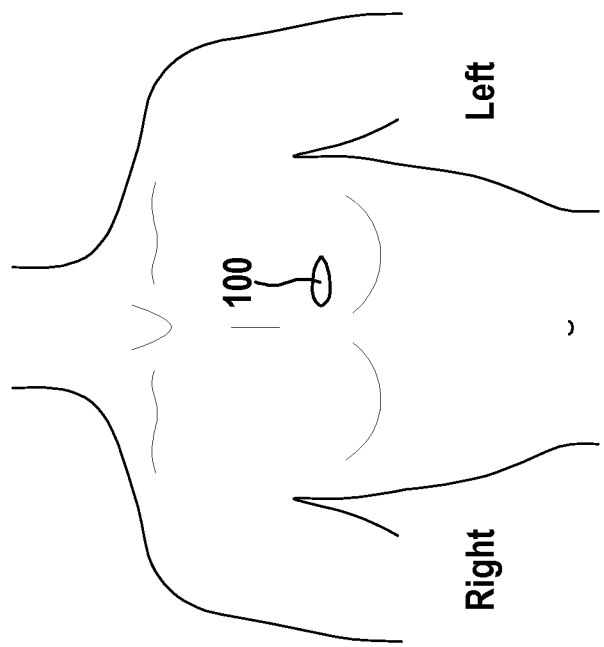

FIG. 16 schematically illustrates two exemplary representative placements for the implantation of an egg-oval shaped embodiment of a cardiac device 100 in a human body. In FIG. 16A, the egg-oval shaped embodiment of the cardiac device 100 (shown in FIG. 14) is implanted in a subcutaneous pocket that is located just to the left side of the sternum. When viewed from the front, the thicker head 99 of the cardiac device 100 in this embodiment points to the sternum and the thinner tail 98 of the cardiac device 100 in this embodiment points to the left side. In FIG. 16B, the egg-oval shaped cardiac device 100 in the embodiment shown in FIG. 15 is implanted in a subcutaneous pocket that is created from the left anterior axillary line. When viewed from the front, the thicker head 98 of the cardiac device 100 in this embodiment points to the left side and the thinner tail 98 of the cardiac device 100 in this embodiment points to the sternum. In both placements, the thicker bottom of the egg-oval shaped embodiments of the cardiac device 100 sits in the pocket and the thinner top of the cardiac device 100 points upward.

Although not shown in above embodiments, it should be understood that in addition to the sensing electrodes 20 mounted on the edge or surface of the subcutaneous implantable cardiac device 100, optionally one or more sensing electrodes 20 may be mounted to one or more short leads (typically with length between 1 cm and 4 cm) that are connected to the implantable cardiac device 100. The extended leads allow further separation of the sensing electrodes 20, thus having the potential to increase the signal-to-noise ratio of the acquired subcutaneous ECG signal.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. A method of enhancing the signal-to-noise ratio (SNR) of measured electrocardiogram (ECG) signals, the method comprising the steps of:
    providing at least three cardiac input signals derived from the measured ECG signals;
    forming a first estimate $U_1$ from each pair of the at least three cardiac input signals;
    forming a second estimate $U_2$ from each of at least three cardiac input signals;
    comparing the polarity and the amplitude of a first and second estimate $U_1$, $U_2$ to at least one threshold T;
    generating a composite signal X, wherein the polarity and the amplitude of the composite signal X depend on the result of the comparison; and using the generated composite signal X to produce an output signal with enhanced signal-to-noise ratio (SNR),
wherein within the step of comparing, the first and second estimate $U_1$ and $U_2$ are compared to an upper threshold UT and a lower threshold LT, wherein the upper threshold UT and the lower threshold LT are different values.

2. The method of claim 1, wherein the first estimate $U_1$ is a differential signal $\tilde{U}$ and the second estimate $U_2$ is an averaged signal $\overline{U}$ formed by using a weighted moving average filter.

3. The method of claim 1, wherein the lower threshold LT and the upper threshold UT are symmetric around the baseline of the measured electrocardiogram (ECG) signals and/or predefinable by a user and/or automatically adjusted based on the moving average of the peaks of the absolute amplitudes of previously measured QRS complexes that are detected within the previously measured electrocardiogram (ECG) signals.

4. The method of claim 1, wherein a composite signal X=0 is generated if the corresponding first estimate $U_1$ is lower than the lower threshold LT and the corresponding second estimate $U_2$ is greater than the upper threshold UT or if the corresponding first estimate $U_1$ is greater than the upper threshold UT and the corresponding second estimate $U_2$ is lower than the lower threshold LT.

5. The method of claim 1, wherein if a first and second estimate $U_1$, $U_2$ are both greater than or equal to the lower threshold LT and both lower than or equal to the upper threshold UT, a corresponding composite signal $X=U_1$ is generated if the absolute value of the corresponding second estimate $U_2$ is greater than the absolute value of the corresponding first estimate $U_1$, or a corresponding composite signal $X=U_2$ is generated if the absolute value of the corresponding first estimate $U_1$ is greater than or equal to the absolute value of the corresponding second estimate $U_2$.

6. The method of claim 1, wherein a composite signal X equal to the arithmetic mean of a corresponding first and second estimate $U_1$, $U_2$ is generated if the corresponding second estimate $U_2$ is greater than or equal to the lower threshold LT and lower than or equal to the upper threshold UT while the corresponding first estimate $U_1$ is either greater than the upper threshold UT or lower than the lower threshold LT or if a corresponding first estimate $U_1$ is greater than or equal to the lower threshold LT and lower than or equal to the upper threshold UT while the corresponding second estimate $U_2$ is either greater than the upper threshold UT or lower than the lower threshold LT.

7. The method of claim 1, wherein if a first and second estimate $U_1$ and $U_2$ are both greater than the upper threshold UT or both lower than the lower threshold LT a corresponding composite signal $X=U_2$ is generated, if the absolute value of the corresponding second estimate $U_2$ is greater than the absolute value of the corresponding first estimate $U_1$, or a corresponding composite signal $X=U_1$ is generated, if the absolute value of the corresponding first estimate $U_1$ is greater than or equal to the absolute value of the corresponding second estimate $U_2$.

8. A cardiac device for use in detecting heartbeats, to which at least three external sensing electrodes are attachable to provide at least three analog voltage input signals, the cardiac device comprising:
an electrocardiogram (ECG) sensing unit for use in producing digital signals from the analog voltage input signals, comprising:
a multiplexer; and
a plurality of signal processing units;
a controller having interconnected parts including a programmable microprocessor, a battery, a memory, a system clock, wherein the battery supplies power to the cardiac device; and
a further processing unit being designed to execute the method of claim 1.

9. The cardiac device of claim 8, wherein the cardiac device comprises a rounded head with a length of $d_1$ and a rounded tail with a length of $d_2$, wherein $d_1$ is smaller than $d_2$.

10. The cardiac device of claim 9, wherein $d_1$ and $d_2$ follow the equation $(d_1+d_2)/d_2 \approx d_2/d_1$ and wherein $d_2/d_1 \approx (1+\sqrt{5})/2 \approx 1.6$.

11. The cardiac device of claim 8, wherein the cardiac device has an asymmetric geometry and resembles a spiral shape, wherein the bottom contour of the cardiac device has a shape that approximates the Fibonacci spiral while the top contour of the cardiac device follows a spiral shape that is rounded at the head and the tail of the cardiac device.

12. The cardiac device of claim 11, wherein the at least three external sensing electrodes are respectively located in the top of the head of the cardiac device, in the bottom of the cardiac device and at the end of the tail of the cardiac device.

13. The cardiac device of claim 8, wherein the cardiac device has an egg-oval shape that is symmetric to a first centerline C1, wherein the head of the cardiac device is wider than the tail of the cardiac device.

14. The cardiac device of claim 13, wherein the cardiac device comprises at least four external sensing electrodes, wherein two of the external sensing electrodes are respectively located with the greatest distance possible from one another, in the tail and the head of the cardiac device, at the intersection points of the first centerline C1 with the circumference of the cardiac device, wherein the other two of the external sensing electrodes are located in the top and bottom of the cardiac device, positioned at the intersection points of a line L1 with the circumference of the cardiac device, wherein the line L1 is orthogonal to the first centerline C1, preferably crossing the center of gravity of the cardiac device.

* * * * *